United States Patent
Parham et al.

(10) Patent No.: US 8,343,637 B2
(45) Date of Patent: Jan. 1, 2013

(54) CARBAZOLE DERIVATIVES FOR ORGANIC ELECTROLUMINESCENT DEVICES

(75) Inventors: Amir Hossain Parham, Frankfurt (DE); Jonas Kroeber, Frankfurt (DE); Arne Buessing, Frankfurt (DE); Horst Vestweber, Gilserberg (DE)

(73) Assignee: Merck Patent GmbH (DE)

( * ) Notice: Subject to any disclaimer, the term of this patent is extended or adjusted under 35 U.S.C. 154(b) by 673 days.

(21) Appl. No.: 12/523,176

(22) PCT Filed: Dec. 10, 2007

(86) PCT No.: PCT/EP2007/010742
§ 371 (c)(1),
(2), (4) Date: Jul. 15, 2009

(87) PCT Pub. No.: WO2008/086851
PCT Pub. Date: Jul. 24, 2008

(65) Prior Publication Data
US 2009/0302752 A1  Dec. 10, 2009

(30) Foreign Application Priority Data

Jan. 18, 2007  (DE) .................. 10 2007 002 714

(51) Int. Cl.
H01L 51/54 (2006.01)
C07D 403/10 (2006.01)

(52) U.S. Cl. ........ 428/690; 428/917; 313/504; 313/506; 548/440; 548/420

(58) Field of Classification Search .................. None
See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 5,840,217 A | 11/1998 | Lupo et al. | |
| 6,458,909 B1 | 10/2002 | Spreitzer et al. | |
| 6,562,982 B1 | 5/2003 | Hu et al. | |
| 6,670,054 B1 | 12/2003 | Hu et al. | |
| 7,345,301 B2 | 3/2008 | Gerhard et al. | |
| 7,482,450 B2 | 1/2009 | Bach et al. | |
| 2003/0186077 A1* | 10/2003 | Chen .................. | 428/690 |
| 2003/0205696 A1 | 11/2003 | Thoms et al. | |
| 2004/0214040 A1* | 10/2004 | Lee et al. ............... | 428/690 |
| 2005/0040390 A1 | 2/2005 | Pfeiffer et al. | |
| 2005/0116622 A1* | 6/2005 | Lo et al. ................ | 313/504 |
| 2006/0175958 A1 | 8/2006 | Gerhard et al. | |
| 2006/0255332 A1 | 11/2006 | Becker et al. | |
| 2007/0034863 A1 | 2/2007 | Fortte et al. | |

FOREIGN PATENT DOCUMENTS

| | | |
|---|---|---|
| EP | 0676461 A2 | 10/1995 |
| EP | 1191612 A2 | 3/2002 |
| EP | 1191613 A2 | 3/2002 |
| EP | 1191614 A2 | 3/2002 |
| EP | 1476881 | 11/2004 |
| EP | 1589787 A2 | 10/2005 |
| EP | 1596445 A1 | 11/2005 |
| EP | 1708547 A1 | 10/2006 |
| JP | 2004288381 A | 10/2004 |
| JP | 2005-093159 * | 4/2005 |
| JP | 2005-183345 * | 7/2005 |
| JP | 2007-123392 * | 5/2007 |
| WO | WO-9827136 A1 | 6/1998 |
| WO | WO-0070655 A2 | 11/2000 |
| WO | WO-0141512 A1 | 6/2001 |
| WO | WO-0202714 A2 | 1/2002 |
| WO | WO-0215645 A1 | 2/2002 |
| WO | WO-03068526 A1 | 8/2003 |
| WO | WO-03070822 A2 | 8/2003 |
| WO | WO-2004085449 A1 | 10/2004 |
| WO | WO-2004093207 A2 | 10/2004 |
| WO | WO-2005003253 A2 | 1/2005 |
| WO | WO-2005011013 A1 | 2/2005 |
| WO | WO-2005016882 A1 | 2/2005 |
| WO | WO-2005033244 A1 | 4/2005 |

OTHER PUBLICATIONS

"Buchwald-Hartwig Cross Coupling Reaction." Organic Chemistry Portal. Web. Jan. 26, 2012. <http://www.organic-chemistry.org/namedreactions/buchwald-hartwig-reaction.shtm>.*
Machine-generated translation for JP 2004-288381, which was published Oct. 2004.*
Chemistry of Materials, (2006), 18(26), pp. 6194-6203.*
Tavasli, Mustafa, et al. "Practical Syntheses of N-Hexylcarbazol-2-yl- and -3-yl-boronic Acids, Their Cross-Coupled Products and a Derived Tris-cyclometalated (Pyridin-2-yl)carbazole Iridium(III) Complex". Synthesis 2005, No. 10, pp. 1619-1624.

* cited by examiner

*Primary Examiner* — Dawn L. Garrett
(74) *Attorney, Agent, or Firm* — Connolly Bove Lodge & Hutz LLP

(57) ABSTRACT

The present invention relates to compounds of the formula (1) and to the use thereof in organic electroluminescent devices, in particular as matrix material in phosphorescent devices.

22 Claims, No Drawings

CARBAZOLE DERIVATIVES FOR ORGANIC ELECTROLUMINESCENT DEVICES

CROSS-REFERENCE TO RELATED APPLICATIONS

This application is a national stage application (under 35 U.S.C. §371) of PCT/EP2007/010742, filed Dec. 10, 2007, which claims benefit of German application 10 2007 002 714.3, filed Jan. 18, 2007.

BACKGROUND OF THE INVENTION

Organic semiconductors are being developed for a number of different applications which can be ascribed to the electronics industry in the broadest sense. The structure of organic electroluminescent devices (OLEDs) in which these organic semiconductors are employed as functional materials is described, for example, in U.S. Pat. Nos. 4,539,507, 5,151, 629, EP 0676461 and WO 98/27136.

A development in recent years is the use of organometallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescence emitters. Whether this development will succeed depends on whether corresponding device compositions are found which are also able to implement these advantages (triplet emission=phosphorescence compared with singlet emission=fluorescence) in the OLEDs.

In general, there are still considerable problems in OLEDs which exhibit triplet emission. Thus, the operating lifetime is generally too short, which has hitherto prevented the introduction of phosphorescent OLEDs ito high-quality and long-lived devices. In phosphorescent OLEDs, the matrix material used is frequently 4,4'-bis(N-carbazolyl)biphenyl (CBP). The disadvantages are short lifetimes of the devices produced therewith and high operating voltages, which result in low power efficiencies. In addition, CBP has an inadequately high glass-transition temperature. In spite of all the disadvantages of CBP, it continues to be used as triplet matrix material, since the problems described above are not solved satisfactorily even using alternative matrix materials.

The object of the present invention is therefore to provide carbazole derivatives which do not have the above-mentioned problems and which have, in particular, a higher glass-transition temperature without thus adversely affecting the other device properties. A further object of the present invention is to provide carbazole derivatives which result in improved efficiencies and lifetimes on use as triplet matrix material in OLEDs.

Surprisingly, it has been found that derivatives of CBP and other carbazole derivatives in which the carbazole is substituted in the 2-position by an aromatic or heteroaromatic group exhibit significant improvements here. In particular, this results in derivatives having a significantly increased glass-transition temperature and in longer lifetimes and higher efficiencies in the device without adversely affecting the other electronic properties of the compound. The present invention therefore relates to these materials and to the use thereof in organic electronic devices.

U.S. Pat. No. 6,562,982 discloses derivatives of CBP which are substituted by aryl groups in the 3,6-position as charge-transport compounds for organic electroluminescent devices. The glass-transition temperatures of these compounds are not indicated. However, the aryl substituents in these compounds are conjugated with the nitrogen of the carbazole and thus have a significant influence on the electronic properties of the compound. It is therefore not possible in this way to obtain CBP derivatives having comparable electronic properties to CBP.

JP 2004/288381 discloses carbazole derivatives which are substituted by fluorinated aromatic compounds as triplet matrix materials. The fluorinated aryl substituents here are bonded to the carbazole in the 2- or 3-position. Due to the high electronegativity of the fluorine, however, these substituents have a strong influence on the electronic properties of the molecule.

BRIEF SUMMARY OF THE INVENTION

The invention relates to a compound of the formula (1)

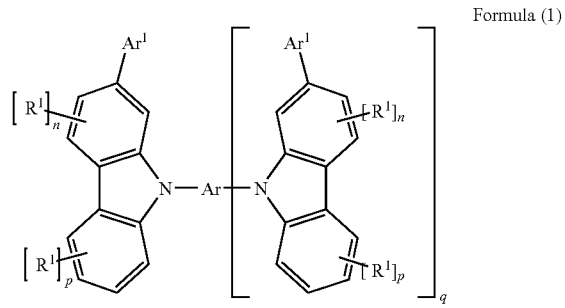

Formula (1)

wherein

Ar is on each occurrence an aromatic or heteroaromatic ring system having 5 to 60 aromatic ring atoms, which is optionally substituted by one or more radicals $R^1$;

$Ar^1$ is on each occurrence, identically or differently, an aromatic or heteroaromatic ring system having 5 to 60 aromatic ring atoms, which is optionally substituted by one or more radicals R;

R is on each occurrence, identically or differently, Cl, Br, I, $N(Ar^2)_2$, CN, $NO_2$, $Si(R^2)_3$, $B(OR^2)_2$, $C(=O)Ar^2$, $P(=O)(Ar^2)_2$, $S(=O)Ar^2$, $-CR^2=CR^2(Ar^2)$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms is optionally replaced by F, Cl, Br, I, CN or $NO_2$, or an aromatic or heteroaromatic ring system having 5 to 60 aromatic ring atoms, which in each case is optionally substituted by one or more radicals $R^2$, or an aryloxy or heteroaryloxy group having 5 to 60 aromatic ring atoms, which is optionally substituted by one or more radicals $R^2$, or a combination of these systems; two or more substituents R here optionally form a mono- or polycyclic aliphatic or aromatic ring system with one another;

$R^1$ is on each occurrence, identically or differently, R, a group $Ar^1$ or F;

$Ar^2$ is on each occurrence, identically or differently, an aromatic or heteroaromatic ring system having 5 to 60 aromatic ring atoms, which is optionally substituted by one or more radicals $R^2$;

$R^2$ is on each occurrence, identically or differently, H or an aliphatic, aromatic and/or heteroaromatic hydrocarbon radical having 1 to 20 C atoms; two or more substituents $R^2$ here optionally form a mono- or polycyclic aliphatic or aromatic ring system with one another;

n is on each occurrence, identically or differently, 0, 1, 2 or 3;

p is on each occurrence, identically or differently, 0, 1, 2, 3 or 4; and q is 1, 2, 3, 4 or 5.

The invention relates to compounds of the formula (1)

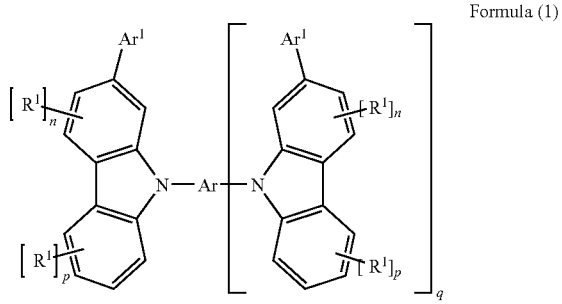

Formula (1)

where the following applies to the symbols and indices used:

Ar is on each occurrence an aromatic or heteroaromatic ring system having 5 to 60 aromatic ring atoms, which may be substituted by one or more radicals $R^1$;

$Ar^1$ is on each occurrence, identically or differently, an aromatic or heteroaromatic ring system having 5 to 60 aromatic ring atoms, which may be substituted by one or more radicals R;

R is on each occurrence, identically or differently, Cl, Br, I, $N(Ar^2)_2$, CN, $NO_2$, $Si(R^2)_3$, $B(OR^2)_2$, $C(=O)Ar^2$, $P(=O)(Ar^2)_2$, $S(=O)Ar^2$, $S(=O)_2Ar^2$, $-CR^2=CR^2$ $(Ar^2)$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2O=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems; two or more substituents R here may also form a mono- or polycyclic aliphatic or aromatic ring system with one another;

R is on each occurrence, identically or differently, R, a group $Ar^1$ or F;

$Ar^2$ is on each occurrence, identically or differently, an aromatic or heteroaromatic ring system having 5 to 60 aromatic ring atoms, which may be substituted by one or more radicals $R^2$;

$R^2$ is on each occurrence, identically or differently, H or an aliphatic, aromatic and/or heteroaromatic hydrocarbon radical having 1 to 20 C atoms; two or more substituents $R^2$ here may also form a mono- or polycyclic aliphatic or aromatic ring system with one another;

n is on each occurrence, identically or differently, 0, 1, 2 or 3;

p is on each occurrence, identically or differently, 0, 1, 2, 3 or 4;

q is 1, 2, 3, 4 or 5.

If the index q is equal to 1, this means that Ar represents a divalent group. If the index q is greater than 1, this means that in total three or more carbazole groups are bonded to the aromatic ring system Ar. Ar is a trivalent group for q=2 and a correspondingly polyvalent group for q>2. The index q is preferably=1 or 2, particularly preferably q=1.

DETAILED DESCRIPTION OF THE INVENTION

The compounds according to the invention preferably have a glass-transition temperature $T_g$ of greater than 120° C., particularly preferably greater than 140° C.

For the purposes of this invention, an aryl group contains 6 to 60 C atoms; for the purposes of this invention, a heteroaryl group contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is to be taken to mean a system which does not necessarily contain only aryl or heteroaryl groups, but instead in which a plurality of aryl or heteroaryl groups may also be interrupted by a non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, etc. are also to be regarded as aromatic ring systems for the purposes of this invention, and likewise systems in which two or more aryl groups are interrupted, for example, by a linear or cyclic alkyl group or by a silyl group. The aromatic ring system preferably contains no metal atoms.

For the purposes of the present invention, a $C_1$- to $C_{40}$-alkyl group, in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methyl-butyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is preferably taken to mean methoxy, trifluoromethoxy, ethoxy, n-propoxy, i-propoxy, n-butoxy, i-butoxy, s-butoxy, t-butoxy or 2-methyl-butoxy. An aromatic or heteroaromatic ring system having 5-60 aromatic ring atoms, which may also in each case be substituted by the above-mentioned radicals R and which may be linked to the aromatic or heteroaromatic ring system via any desired positions, is taken to mean, in particular, groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred embodiment of the invention, the indices n in compounds of the formula (1) are on each occurrence, identically or differently, 0 or 1. The indices n are particularly preferably=0.

Preferred structures of the formula (1) are the compounds of the formulae (2) to (7):

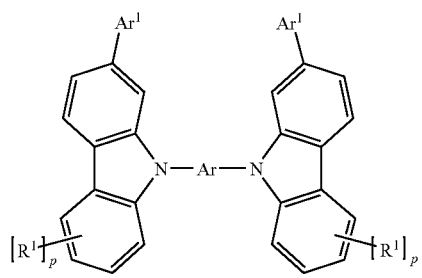

Formula (2)

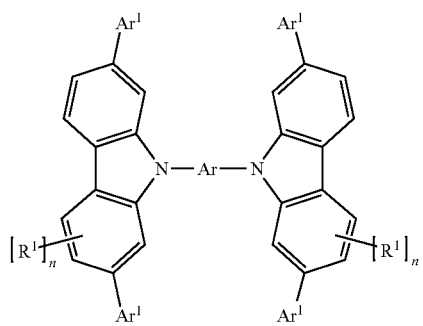

Formula (3)

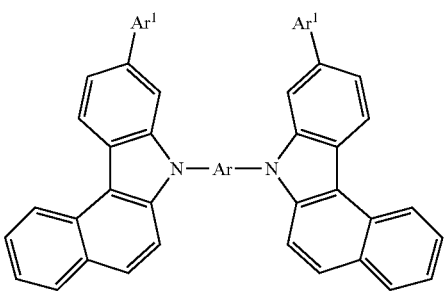

Formula (4)

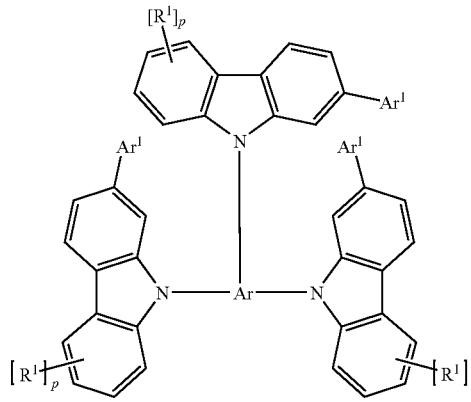

Formula (5)

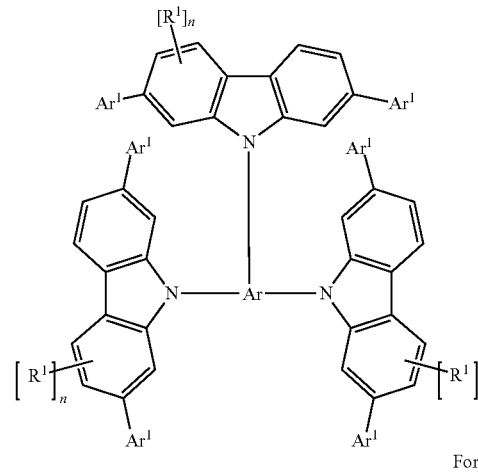

Formula (6)

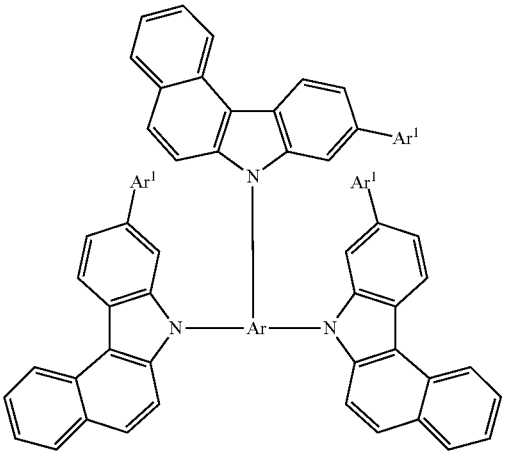

Formula (7)

where the symbols and indices have the meanings indicated above.

In a preferred embodiment of the compounds of the formula (1) or of the formula (2) or formula (5), the index p is, identically or differently on each occurrence, 0, 1 or 2, particularly preferably 0 or 1. If the index p is equal to 1, the substituent $R^1$ is preferably bonded in the 5-position or 7-position of the carbazole, particularly preferably in the 5-position. If the index p is equal to 2, the substituents $R^1$ are preferably bonded in the 5- and 7-position of the carbazole.

In a preferred embodiment of the compounds of the formula (3) or formula (6), the index n is, identically or differently on each occurrence, 0 or 1. If the index n is equal to 1, the substituent $R^1$ is preferably bonded in the 5-position of the carbazole.

For reasons of clarity, the numbering of the positions of the carbazole is depicted in the following formula:

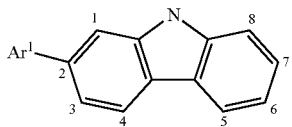

Preferred groups Ar and $Ar^1$ in formula (1) or in formulae (2) to (7) contain only phenyl and/or naphthyl groups or heteroaromatic groups having not more than two condensed aromatic or heteroaromatic rings, but no larger condensed aromatic systems. Preferred groups Ar and $Ar^1$ are therefore aromatic ring systems built up from phenyl and/or naphthyl groups or linked systems of this type, such as, for example, biphenyl, fluorene, spirobifluorene, etc. The group Ar or $Ar^1$ is furthermore preferably carbazole.

Particularly preferred groups Ar are selected from 1,2-phenylene, 1,3-phenylene, 1,4-phenylene, 1,3,5-benzene, 3,3'-biphenyl, 4,4'-biphenyl, 1,3,5-triphenylbenzene, triphenylamine, 2,7-fluorenylene, which may be substituted by one or more radicals $R^1$, 2,7-spirobifluorenylene, which may be substituted by one or more radicals $R^1$, indenofluorenylene, which may be substituted by one or more radicals $R^1$, 4,4'''-(1, 1':2',1'',2'',1'''-quaterphenyl), 4,4'-(2,2'-dimethylbiphenyl), 4,4'-(1,1'-binaphthyl), 4,4'-stilbenyl or dihydrophenanthrenyl, which may be substituted by one or more radicals $R^1$.

Particularly preferred groups $Ar^1$ are selected, identically or differently, from phenyl, 1-naphthyl, 2-naphthyl, 2-carbazolyl, 3-carbazolyl, 9-carbazolyl, triphenylamine, naphthyldiphenylamine or dinaphthylphenylamine, each of which may be substituted by one or more radicals R. The two last-mentioned groups here may be bonded via the naphthalene in the 1- or 2-position or via the phenyl group A 2- or 3-carbazolyl group here is preferably substituted on the nitrogen by an aromatic radical R.

Preference is furthermore given to compounds of the formula (1) or compounds of the formulae (2) to (7) in which the symbol R, i.e. the substituent on the group $Ar^1$, stands, identically or differently on each occurrence, for H, $N(Ar^2)_2$, a straight-chain alkyl group having 1 to 5 C atoms or branched alkyl group having 3 to 5 C atoms, where in each case one or more non-adjacent $CH_2$ groups may be replaced by —$R^2C$=$CR^2$— or —O— and where one or more H atoms may be replaced by F, or an aryl group having 6 to 16 C atoms or a heteroaryl group having 2 to 16 C atoms or a spirobifluorene group, each of which may be substituted by one or more radicals $R^2$, or a combination of two of these systems. Particularly preferred radicals R are, identically or differently on each occurrence, H, methyl, ethyl, isopropyl, tert-butyl, where in each case one or more H atoms may be replaced by F, or a phenyl, naphthyl or spirobifluorenyl group, each of which may be substituted by one or more radicals $R^2$, or a combination of two of these systems. In compounds which are processed from solution, linear or branched alkyl chains having up to 10 C atoms are also preferred. Bromine, boronic acid or boronic acid derivatives as substituents are particularly preferred for use of this compound as intermediate compound for the preparation of further compounds according to the invention.

Preference is furthermore given to compounds of the formula (1) or compounds of the formulae (2) to (7) in which the symbol $R^1$ is defined, identically or differently on each occurrence, in accordance with the preferred substituent R or stands for $Ar^1$ or F.

Preference is furthermore given to symmetrical compounds, i.e. compounds in which all symbols $Ar^1$ are identical and are identically substituted.

Examples of preferred compounds of the formula (1) are compounds (1) to (72) depicted below:

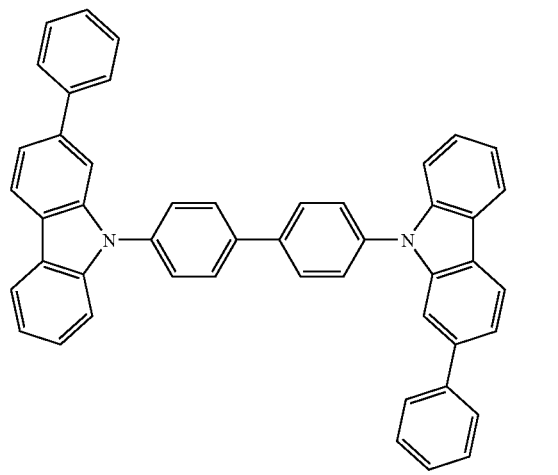

(1)

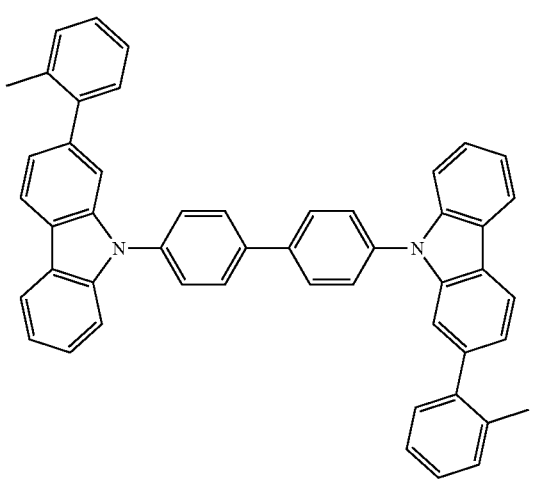

(2)

(3)
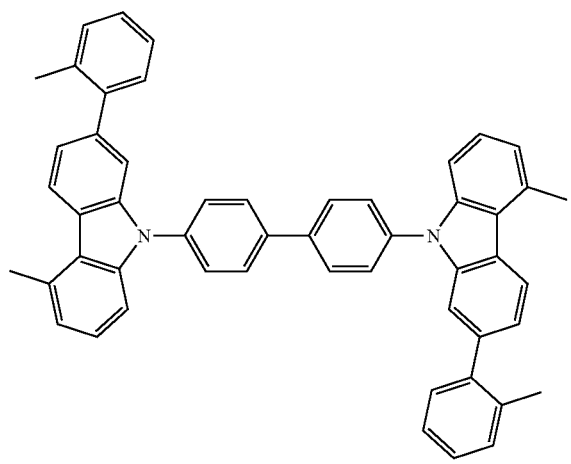
(4)
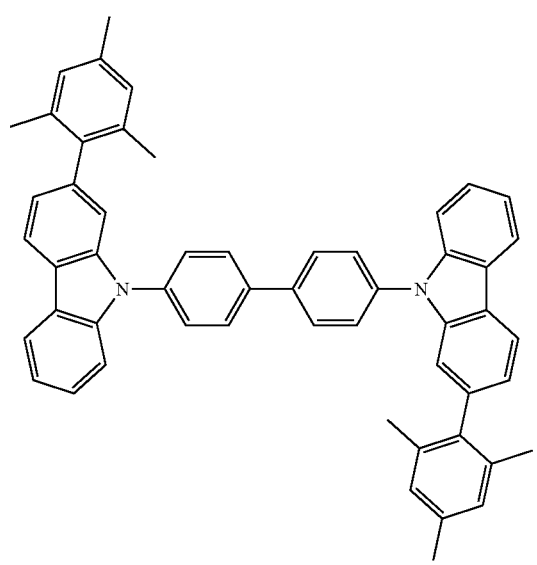
(5)
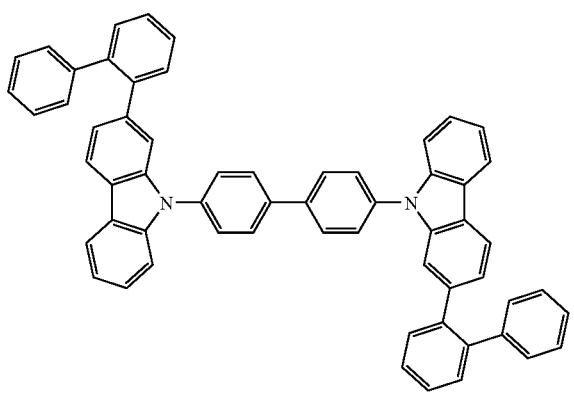
(6)
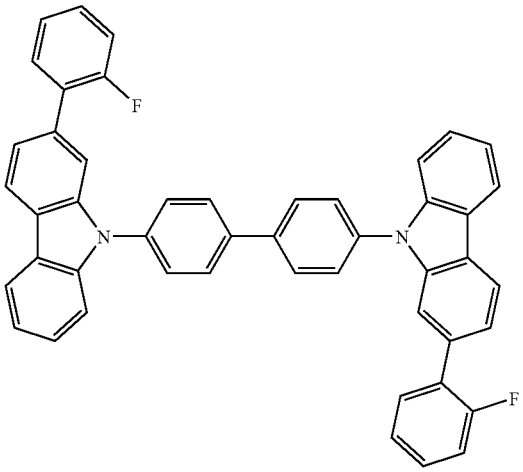
(7)
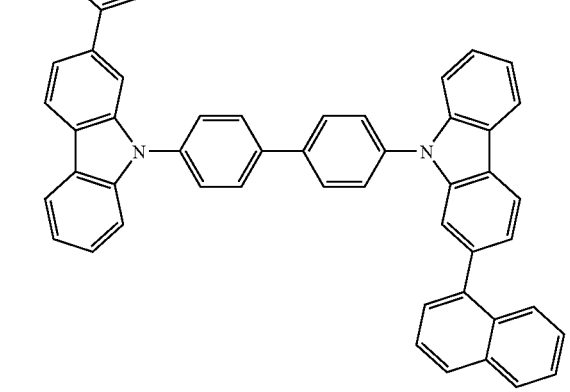
(8)
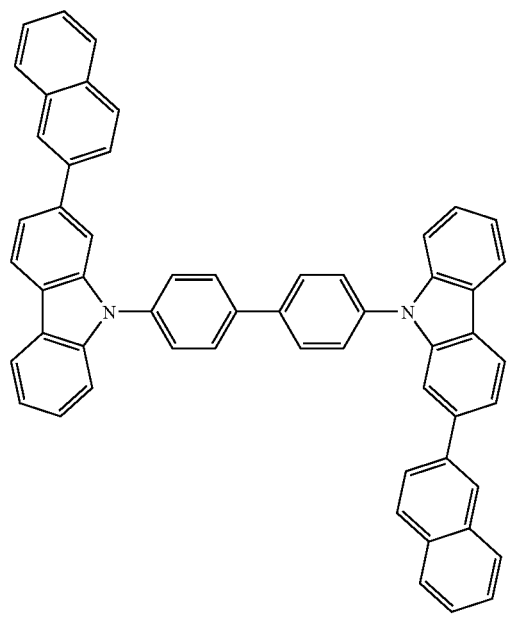

-continued
(9)
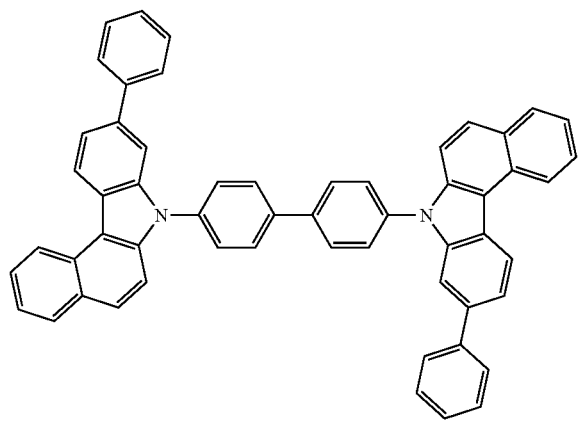
(10)
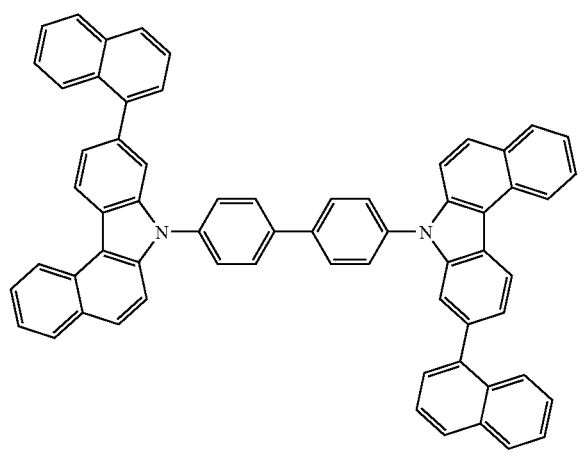
(11)
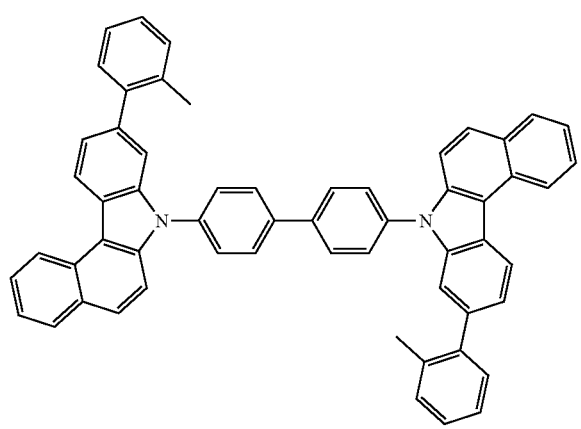
(12)
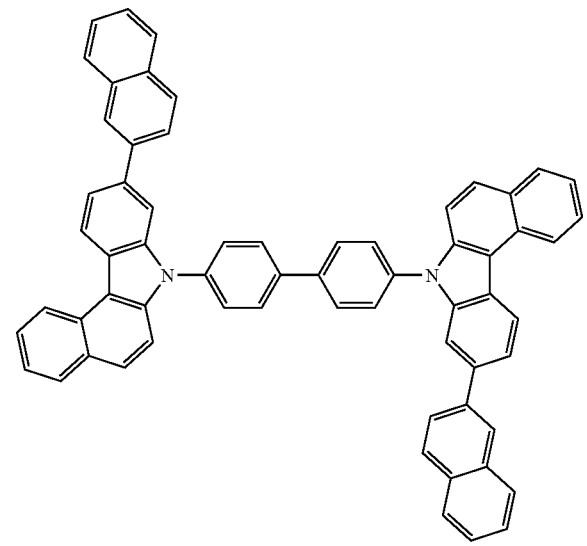
(13)
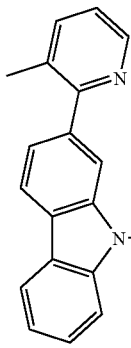
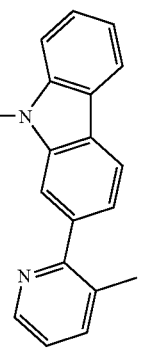
(14)
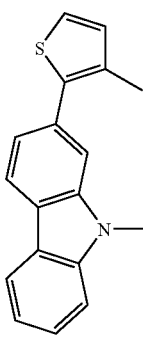
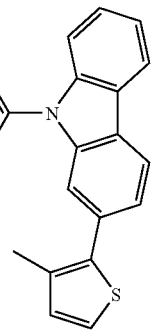

(15)
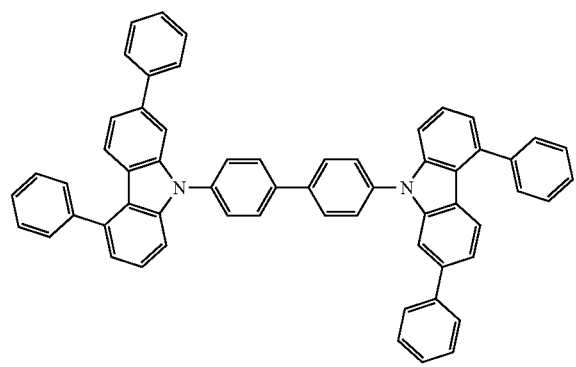
(16)
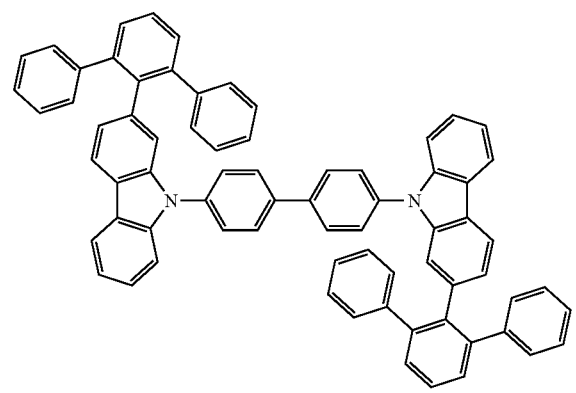
(17)
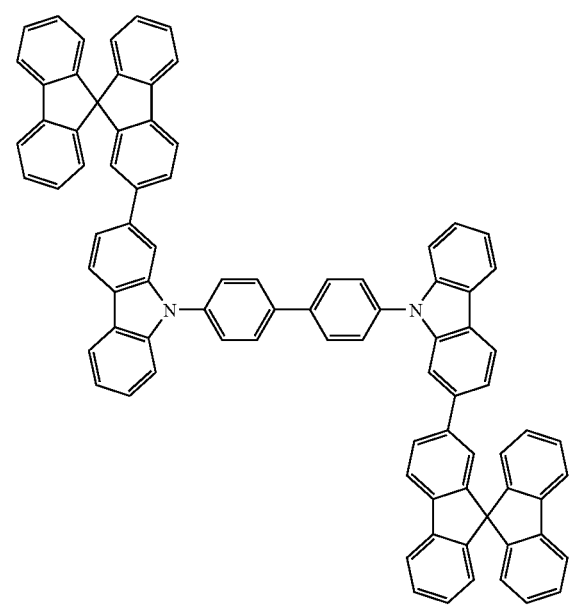
(18)
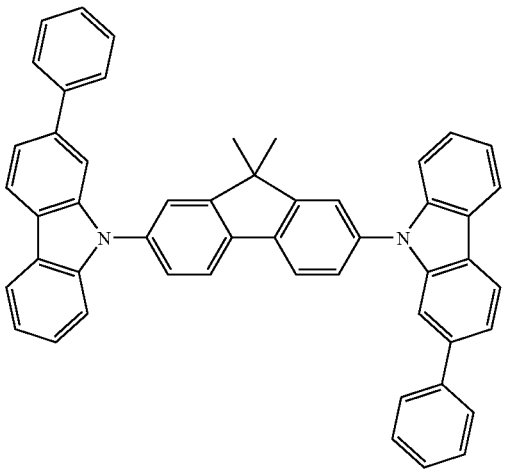
(19)
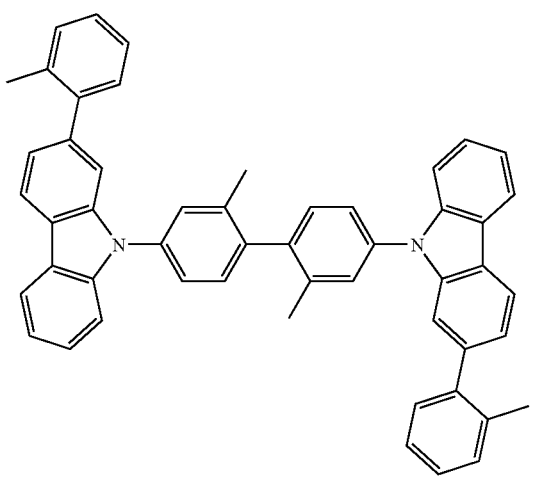
(20)
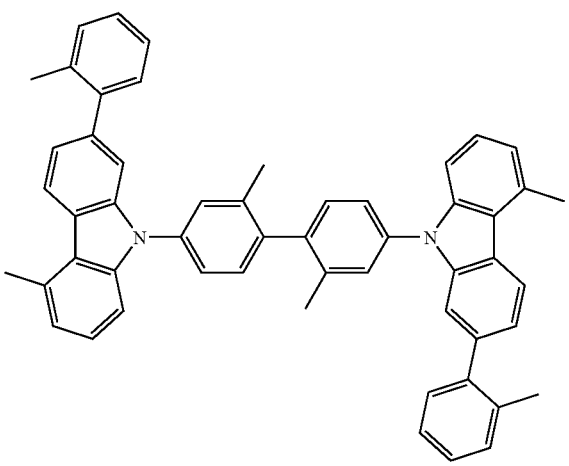

(21)
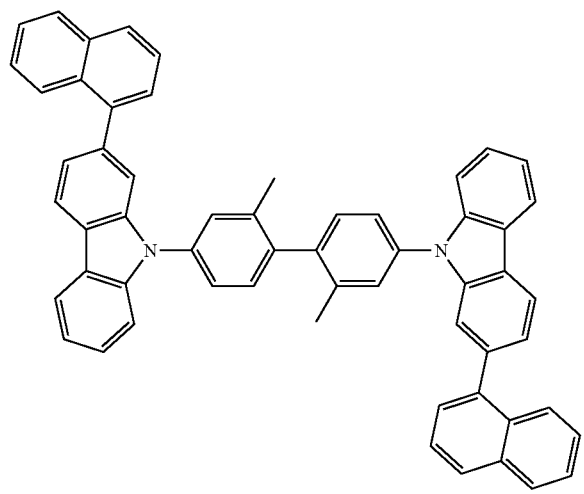
(24)
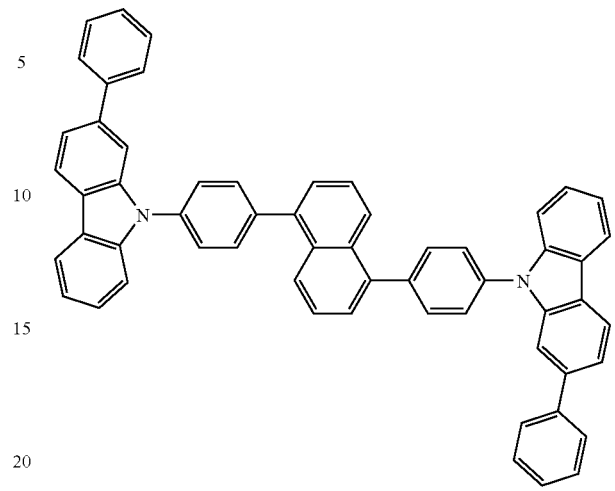
(22)
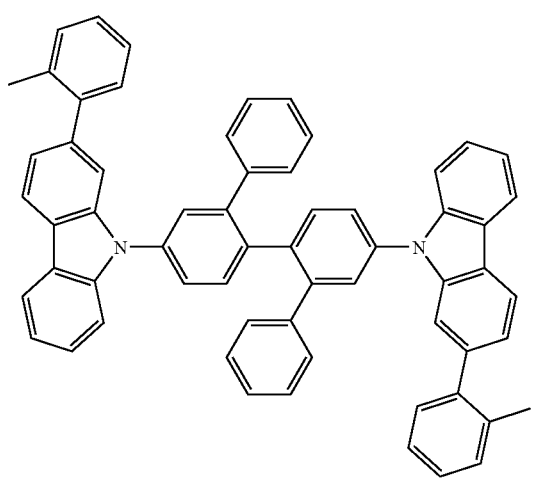
(25)
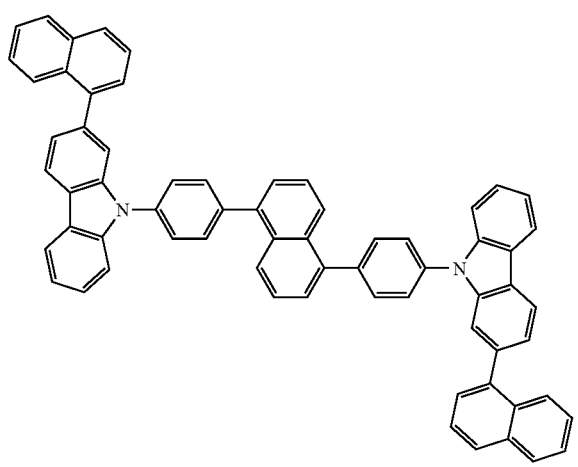
(23)
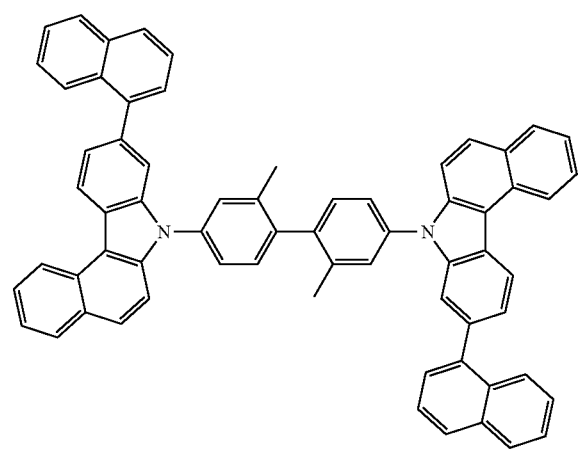
(26)
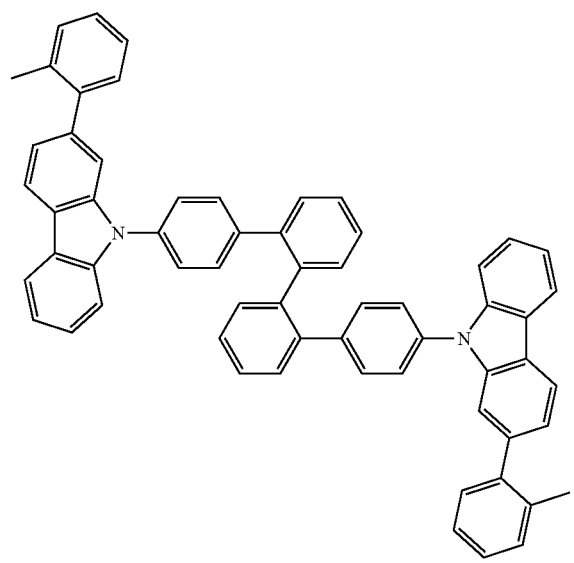

(27)
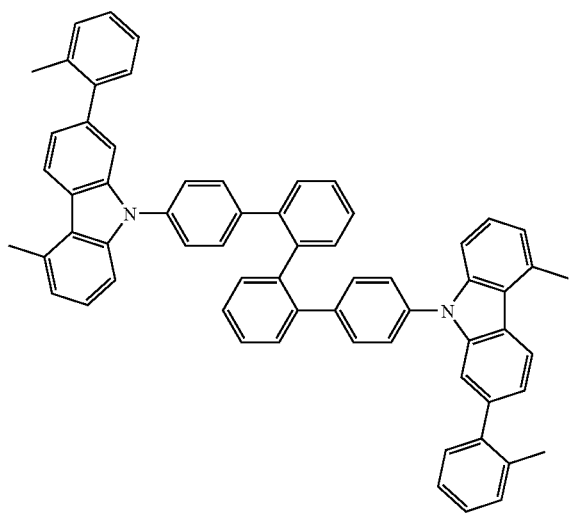
(28)
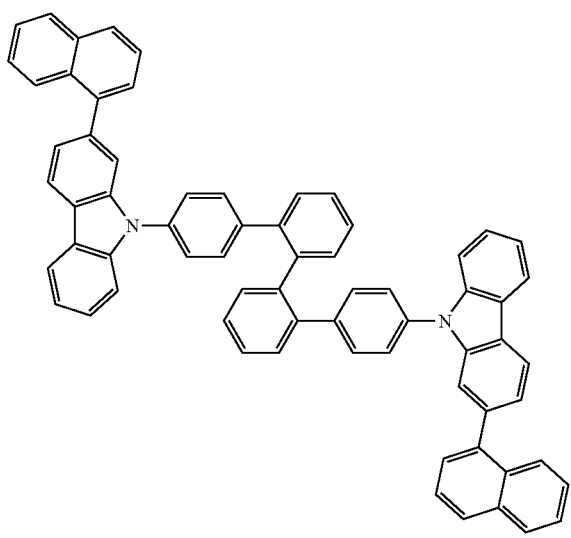
(29)
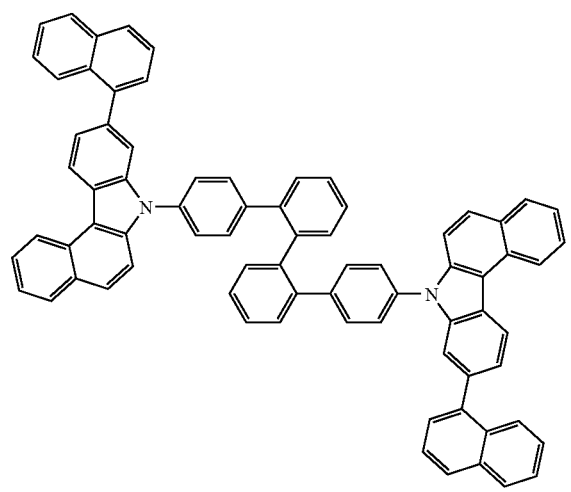
(30)
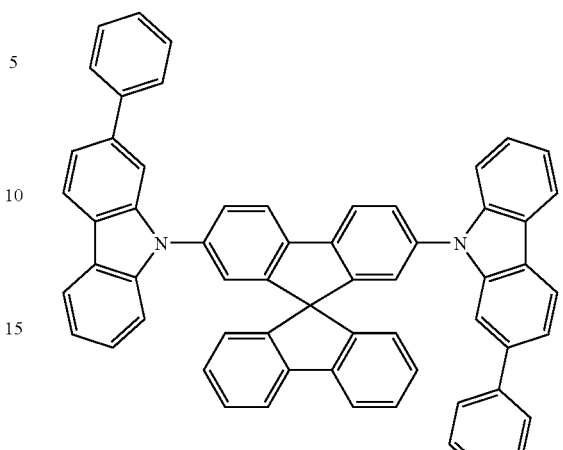
(31)
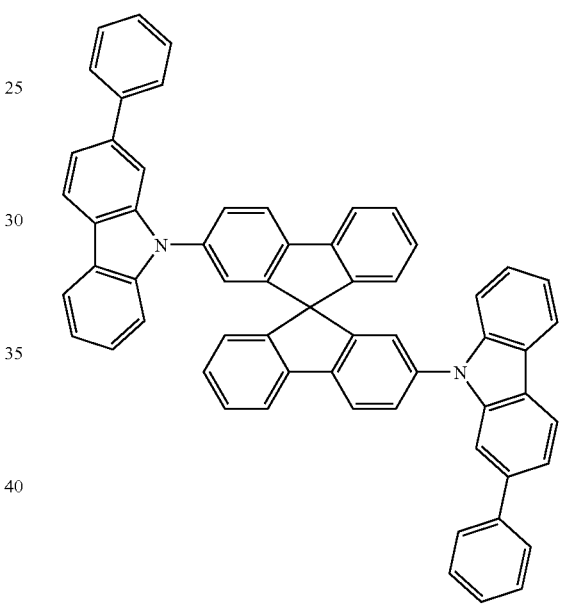
(32)
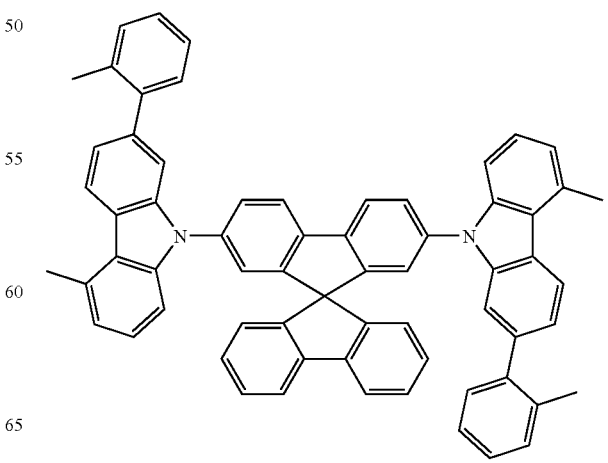

(33)
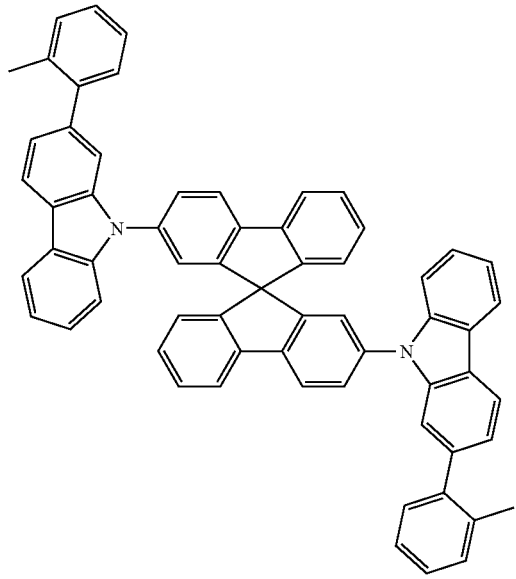
(34)
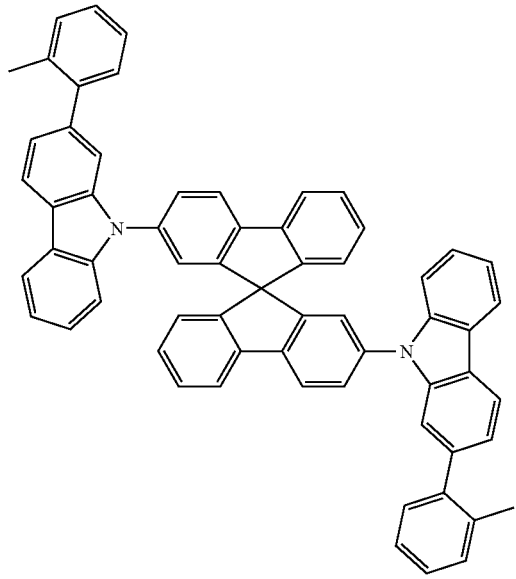
(35)
(36)
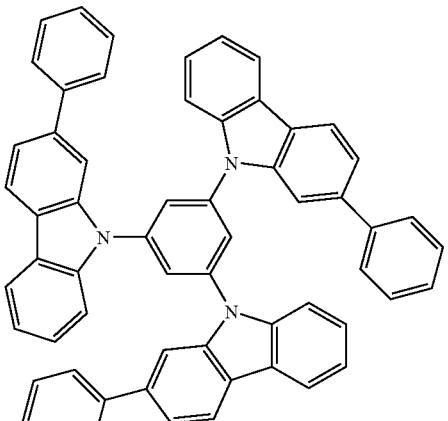
(37)
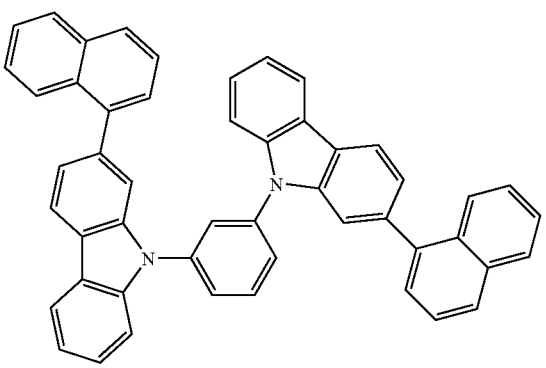
(38)
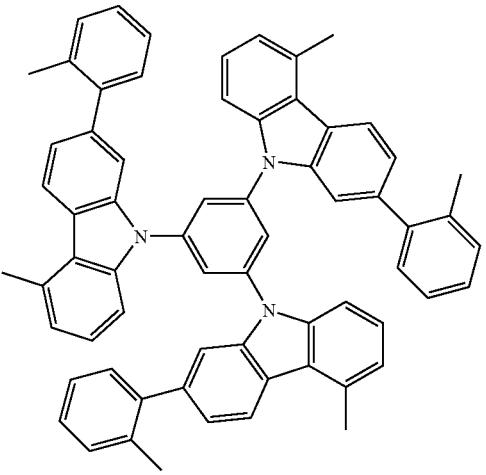
(39)
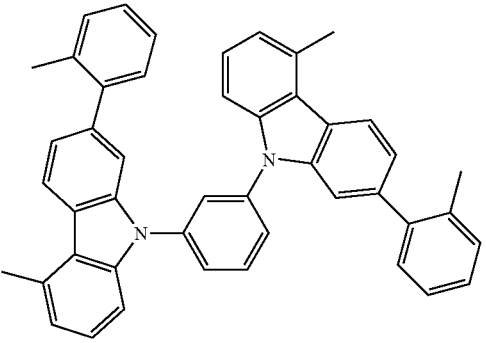

(40)
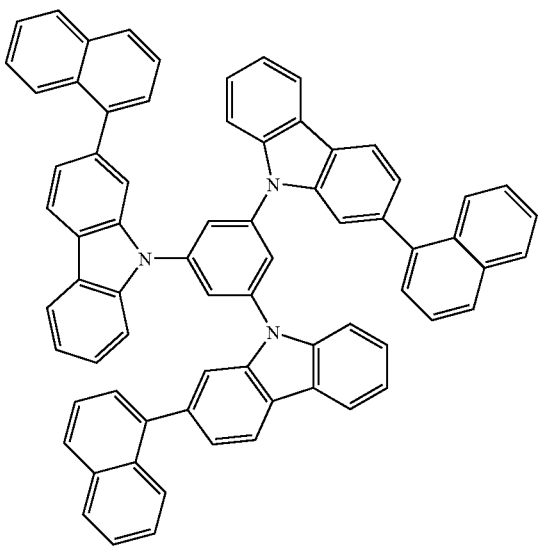
(43)
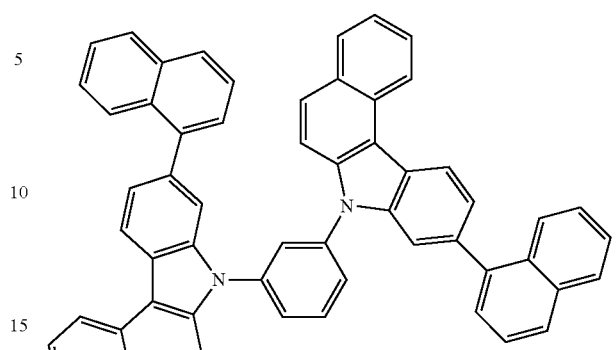
(41)
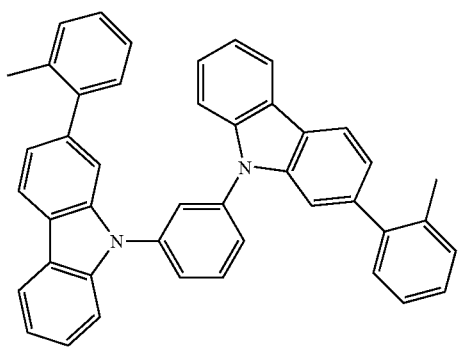
(44)
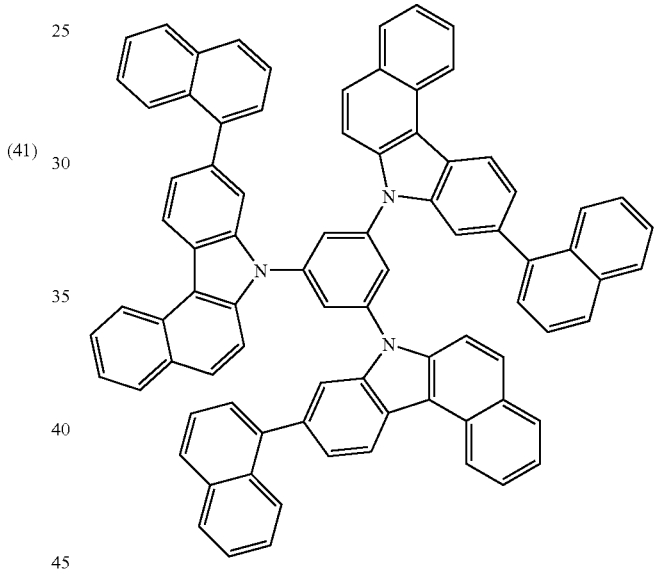
(42)
(45)
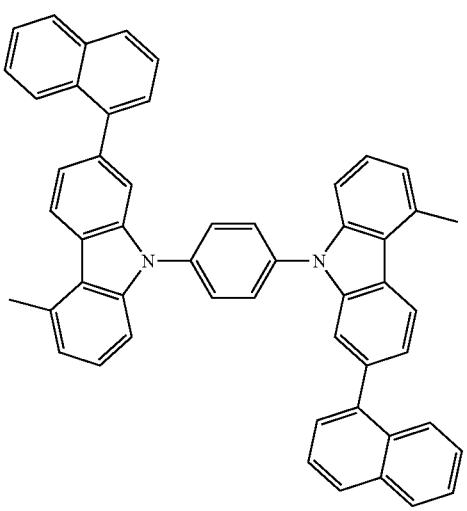

-continued
(46)
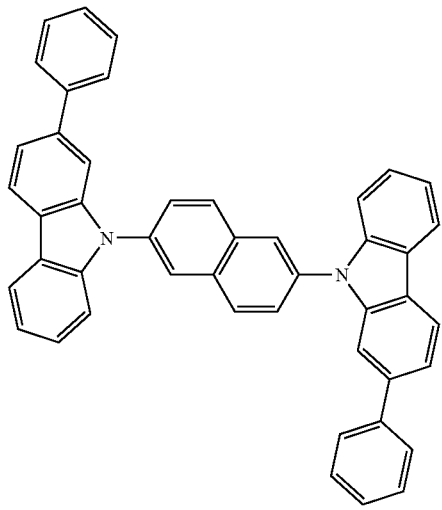
(47)
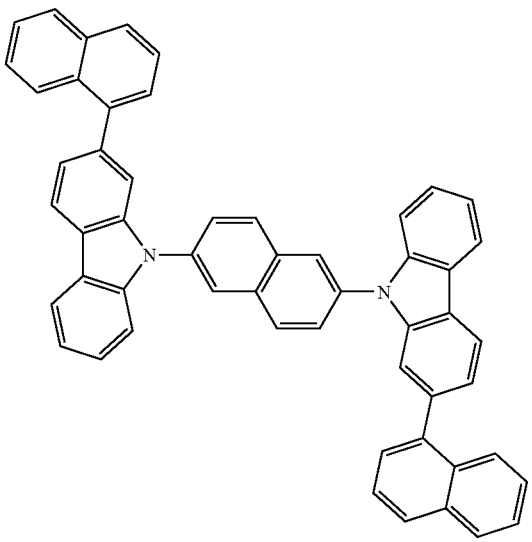
(48)
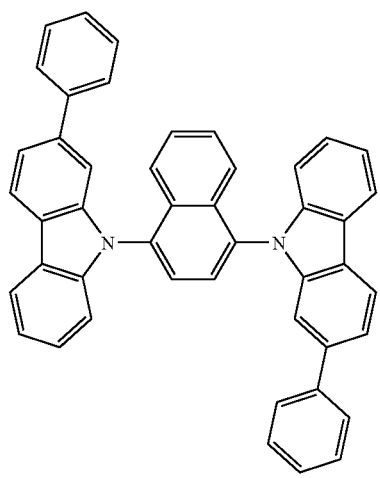
(49)
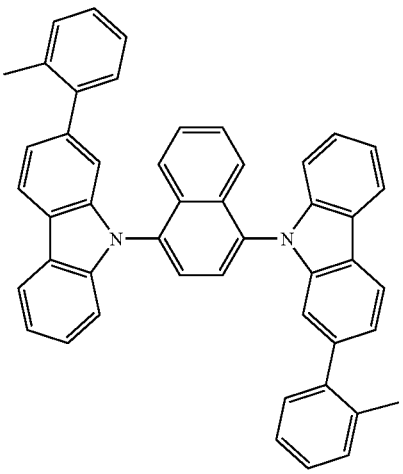
(50)
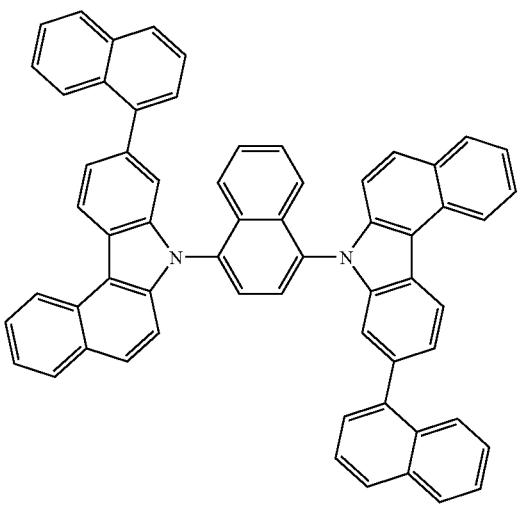
(51)
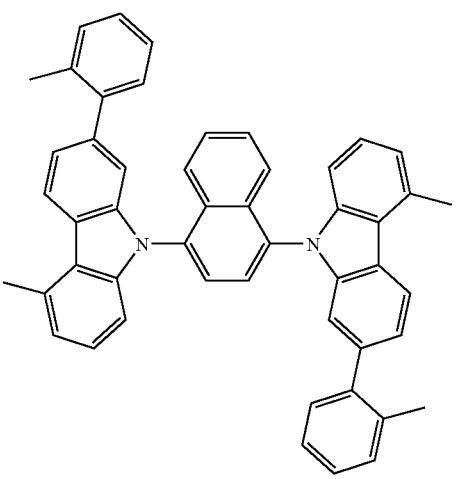

(52)
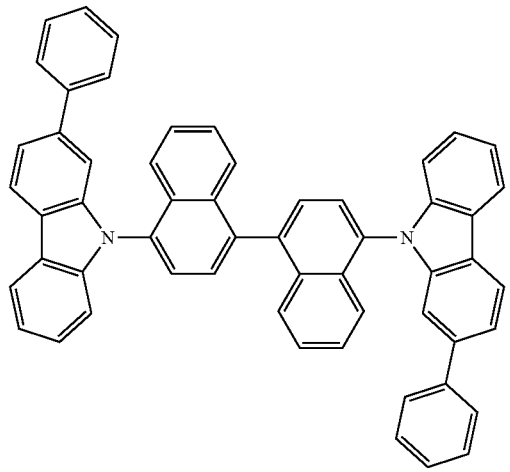
(55)
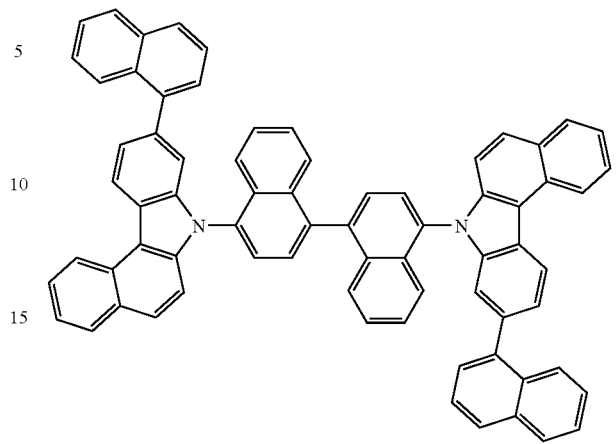
(53)
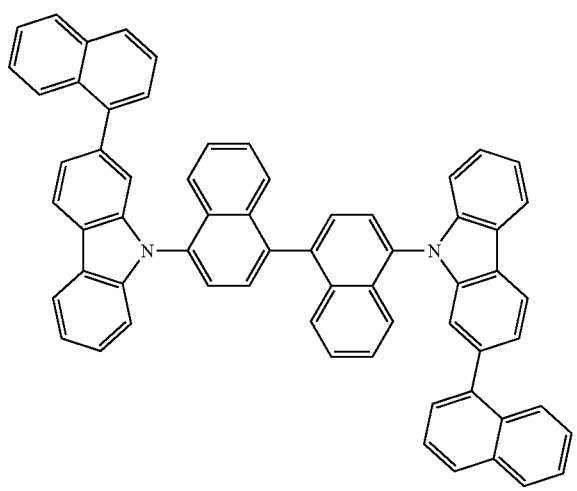
(56)
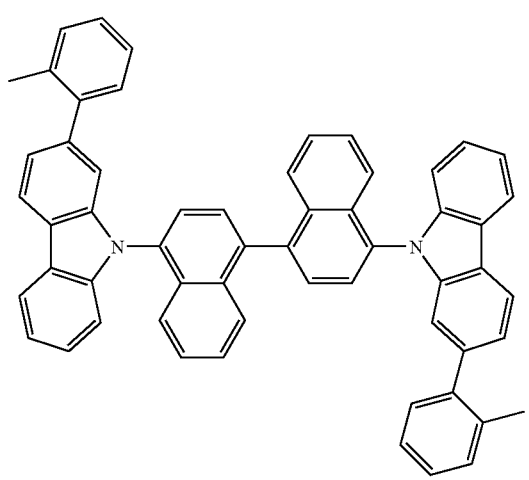
(54)
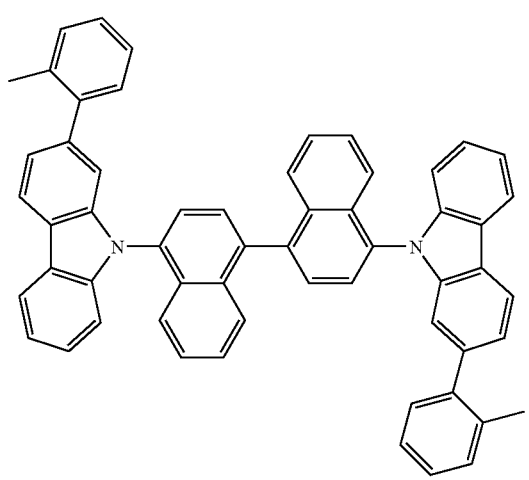
(57)
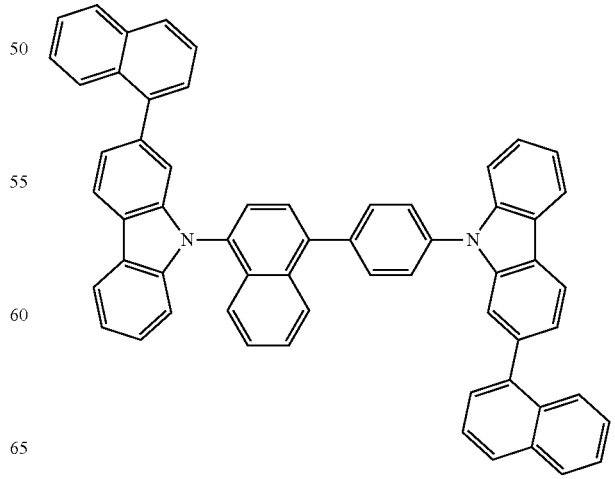

(58)
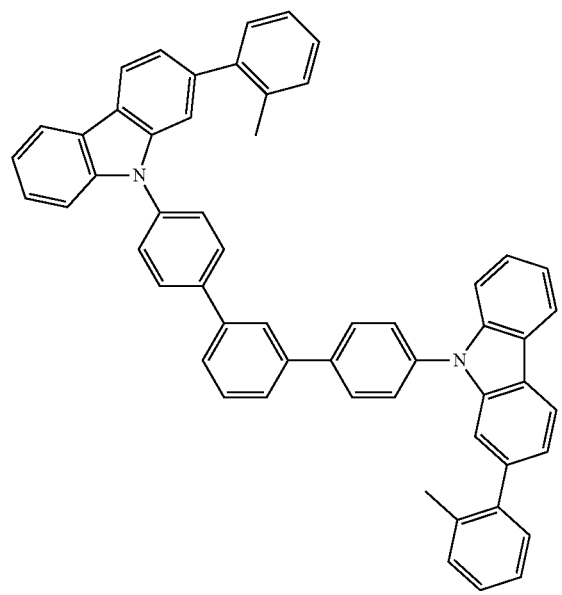
(59)
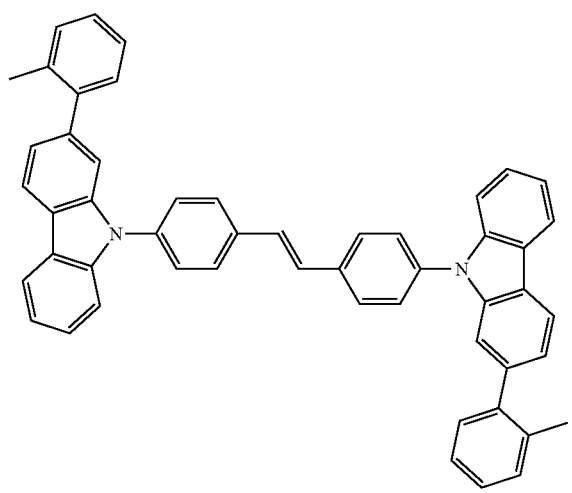
(60)
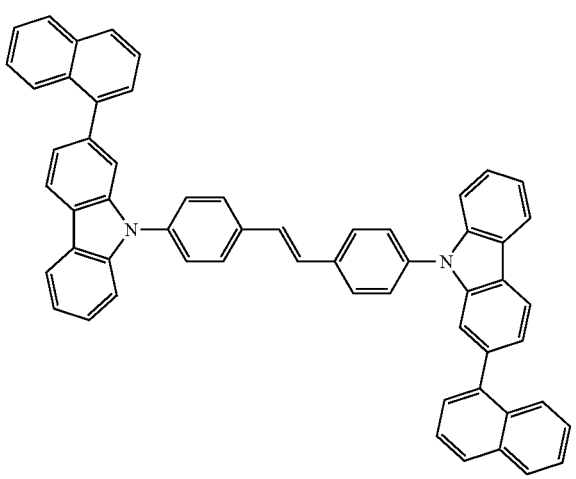
(61)
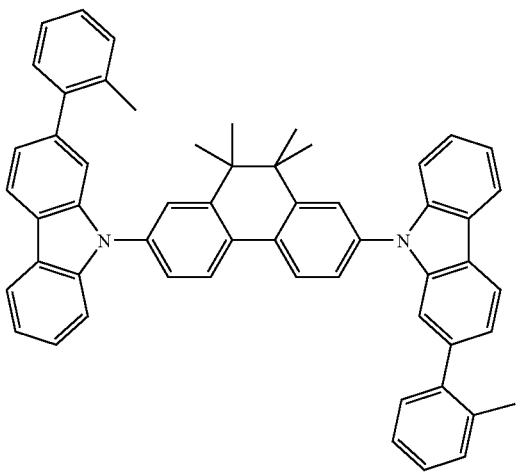
(62)
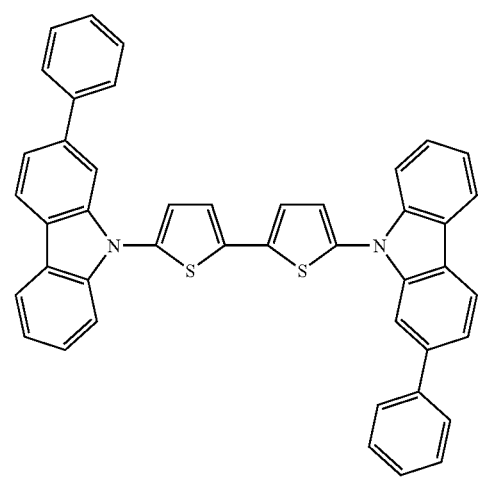
(63)
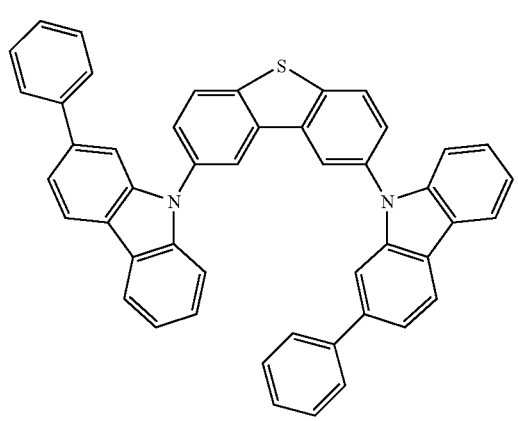

(64)
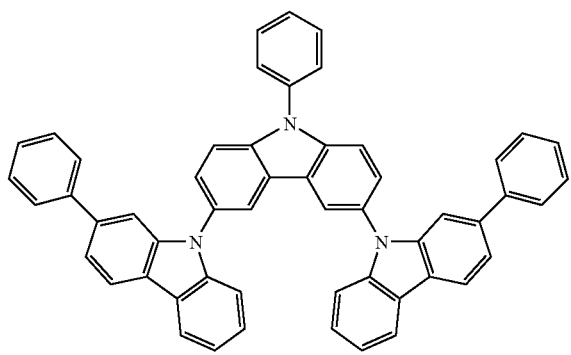
(65)
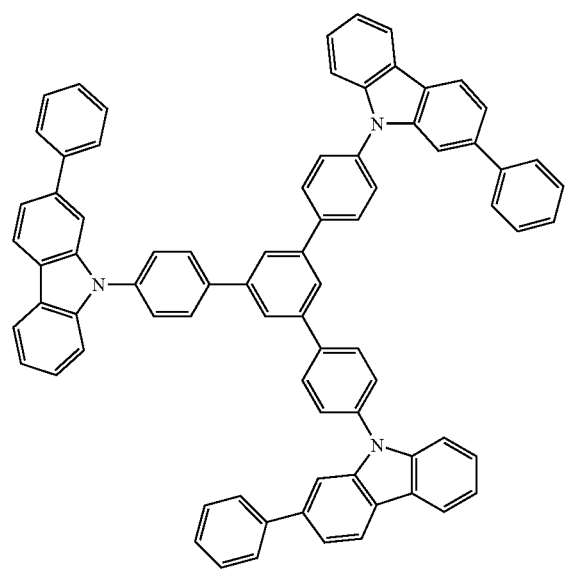
(66)
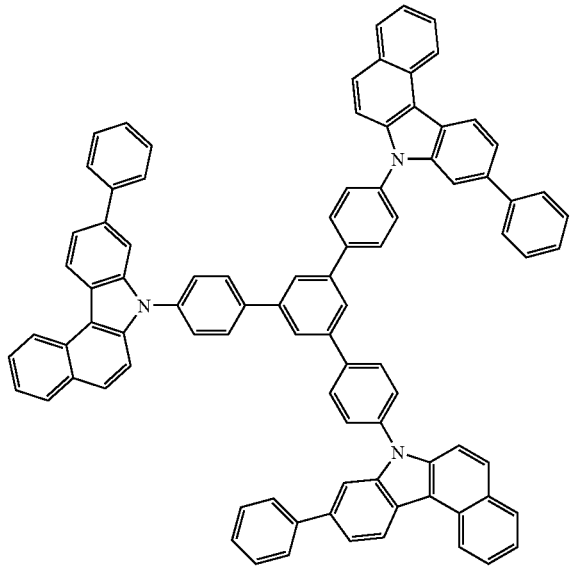
(67)
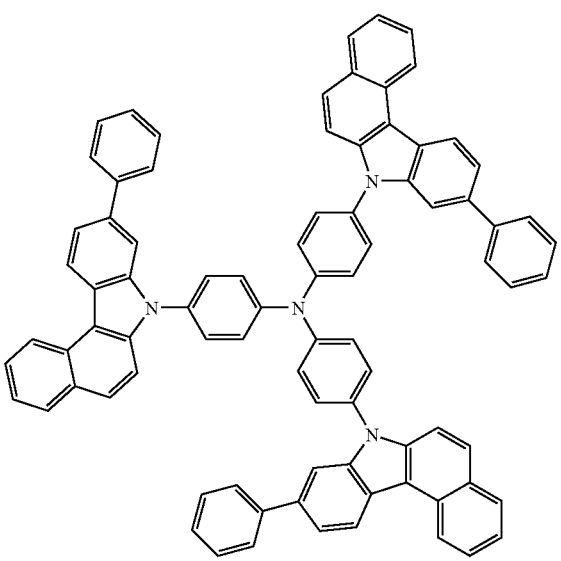
(68)
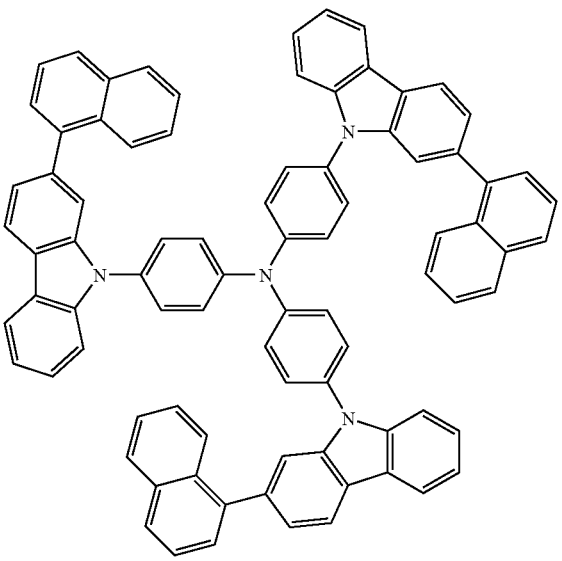
(69)
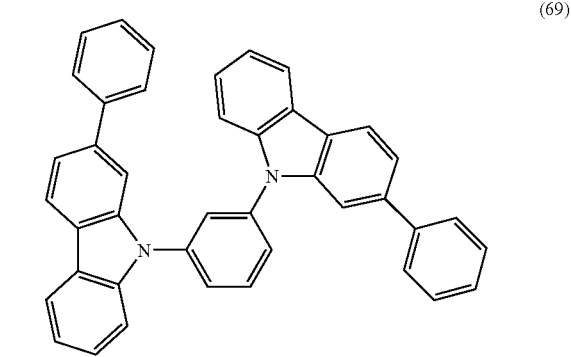

(70)

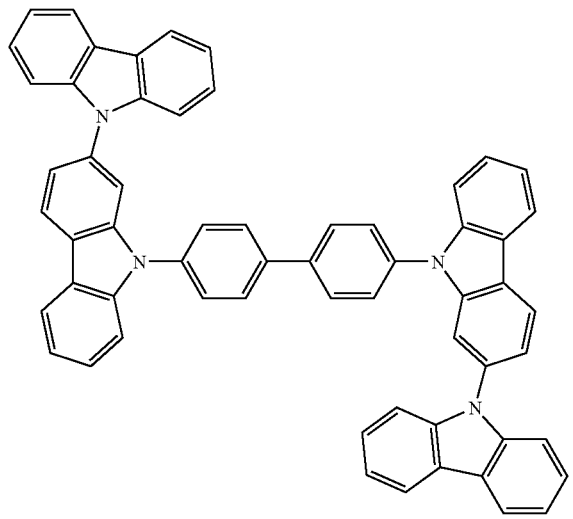

(71)

(72)

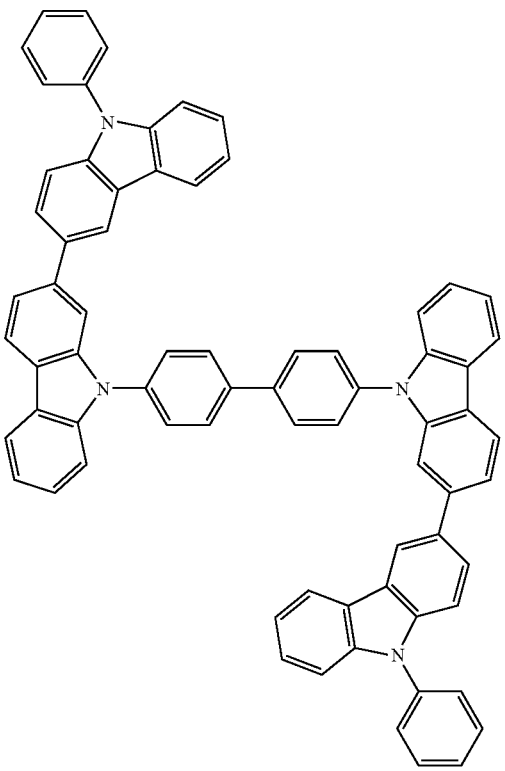

The compounds according to the invention can be synthesised by standard methods of organic chemistry Thus, it is known that 2-nitrobiphenyl derivatives can be reacted with a trialkyl phosphite to give the corresponding carbazole derivatives (M. Tavasli et al., *Synthesis* 2005, 1619-1624). This reaction can be used to build up 2-aryl-substituted carbazole derivatives by firstly building up a corresponding aryl-substituted 2-nitrobiphenyl derivative, which is subsequently reacted with trialkyl phosphite. The 2-aryl-substituted carbazole derivative can be coupled to a dibrominated aromatic compound in a Hartwig-Buchwald coupling under standard conditions to give the compound of the formula (1). The various methods for carrying out the Hartwig-Buchwald coupling and the various reaction conditions therein are known to the person skilled in the art of organic synthesis. Instead of a dibrominated aromatic compound, it is also possible to use corresponding compounds containing different leaving groups, for example chlorine, iodine, triflate, tosylate or generally sulfonates. The use of trisubstituted aromatic compounds or compounds containing still more leaving groups enables the corresponding synthesis of compounds of the formula (1) in which the index q stands for 2 or more.

The synthesis of compounds of the formula (1) is depicted in scheme 1 below, where, for reasons of clarity, q has been selected to be=1, and no substituents R or $R^1$ are shown:

Scheme 1:

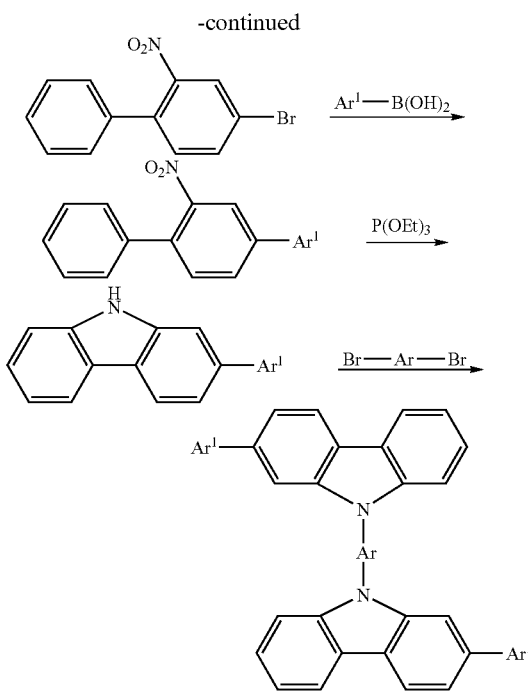

The present invention furthermore relates to a process for the preparation of compounds of the formula (1), starting from a 4-aryl-2-nitro-1,1'-biphenyl or 4-heteroaryl-2-nitro-1,1'-biphenyl, where the aryl group or heteroaryl group may also be substituted by one or more radicals R and the biphenyl may also be substituted by one or more radicals $R^1$, which is reacted with a trialkyl phosphite, where the alkyl groups, identically or differently on each occurrence, have 1 to 10 C atoms, to give the corresponding carbazole, followed by a Hartwig-Buchwald coupling to an aromatic compound which has at least two reactive groups. The reactive groups for the Hartwig-Buchwald coupling are preferably selected from chlorine, bromine, iodine, triflate, tosylate or $OSO_2$—$R^2$, where $R^2$ has the same meaning as indicated above.

The compounds according to the invention are suitable for use in organic electroluminescent devices (OLEDs, PLEDs), in particular as triplet matrix materials in phosphorescent OLEDs, but also as hole-transport materials.

The invention therefore furthermore relates to the use of compounds of the formula (1) in organic electronic devices, in particular in organic electroluminescent devices.

Moreover, the invention furthermore relates to organic electronic devices comprising at least one compound of the formula (1), in particular organic electroluminescent devices, comprising anode, cathode and at least one emitting layer, characterised in that at least one layer comprises at least one compound of the formula (1).

Apart from cathode, anode and the emitting layer, the organic electroluminescent device may also contain further layers, for example in each case one or more hole-injection layers, hole-transport layers, hole-blocking layers, electron-transport layers, electron-injection layers and/or charge-generation layers (IDMC 2003, Taiwan; Session 21 OLED (5), T. Matsumoto, T. Nakada, J. Endo, K. Mori, N. Kawamura, A. Yokoi, J. Kido, *Multi-photon Organic EL Device Having Charge Generation Layer*). Interlayers which have, for example, an exciton-blocking function may likewise be introduced between two emitting layers. However, it should be pointed out that each of these layers does not necessarily have to be present.

In a further preferred embodiment of the invention, the organic electroluminescent device contains a plurality of emitting layers, where at least one layer comprises at least one compound according to the invention. The emission layers particularly preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where at least one of these layers comprises at least one compound according to the invention and where the three layers exhibit blue, green and orange or red emission (for the basic structure, see, for example, WO 05/011013). Emitters which have broad-band emission bands and thus exhibit white emission are likewise suitable for white emission.

In a preferred embodiment of the invention, the compounds according to the invention are employed as matrix for phosphorescent dopants. For the purposes of this invention, phosphorescence here is taken to mean luminescence from an excited state of relatively high spin multiplicity, in particular luminescence from an excited triplet state. The phosphorescent dopants comprise at least one compound which emits light, preferably in the visible region, on suitable excitation and in addition contains at least one atom having an atomic number of greater than 20, preferably greater than 38 and less than 84, particularly preferably greater than 56 and less than 80. The phosphorescence emitters are preferably compounds which contain copper, molybdenum, tungsten, rhenium, ruthenium, osmium, rhodium, iridium, palladium, platinum, silver, gold or europium, in particular compounds which contain iridium or platinum. Emitters of this type are known to the person skilled in the art in the area of electroluminescence.

Particularly preferred organic electroluminescent devices comprise, as phosphorescent emitter, at least one compound of the formulae (8) to (11)

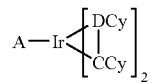 Formula (8)

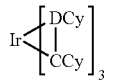 Formula (9)

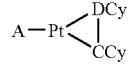 Formula (10)

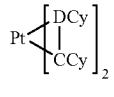 Formula (11)

where the following applies to the symbols used:
DCy is, identically or differently on each occurrence, a cyclic group which contains at least one donor atom, preferably nitrogen or phosphorus, via which the cyclic group is bonded to the metal, and which may in turn carry one or more substituents $R^1$; the groups DCy and CCy are bonded to one another via a covalent bond;
CCy is, identically or differently on each occurrence, a cyclic group which contains a carbon atom via which the cyclic group is bonded to the metal and which may in turn carry one or more substituents $R^1$;

A is, identically or differently on each occurrence, a monoanionic, bidentate, chelating ligand, preferably a diketonate ligand;

$R^1$ has the same meaning as described above.

A bridge may also be present here between the groups DCy and CCy due to the formation of ring systems between a plurality of radicals $R^1$.

Examples of the emitters described above are revealed by the applications WO 00/70655, WO 01/41512, WO 02/02714, WO 02/15645, EP 1191613, EP 1191612, EP 1191614 and WO 05/033244.

In general, phosphorescent complexes as used in accordance with the prior art for phosphorescent OLEDs and as are generally known to the person skilled in the art are suitable.

The mixture according to the invention comprises between 1 and 99% by weight, preferably between 2 and 90% by weight, particularly preferably between 3 and 40% by weight, in particular between 5 and 15% by weight, of the phosphorescent emitter, based on the entire mixture of emitter and matrix materials. Correspondingly, the mixture according to the invention comprises between 99 and 1% by weight, preferably between 98 and 10% by weight, particularly preferably between 97 and 60% by weight, in particular between 95 and 85% by weight, of the matrix material or matrix materials, based on the entire mixture of emitter and matrix materials.

The compound of the formula (1) can either be the only matrix material in the emitting layer. However, it is also possible to use a mixture of a plurality of matrix materials in the emitting layer. These can be a plurality of different matrix materials of the formula (1). It has furthermore proven preferable to employ a matrix material of the formula (1) together with an aromatic ketone or an aromatic phosphine oxide, an aromatic sulfoxide or an aromatic sulfone as further matrix material and a phosphorescent dopant in the emitting layer. Preferred aromatic ketones are those in which two aromatic or heteroaromatic ring systems are bonded to the keto group. Preferred aromatic phosphine oxides are those in which three aromatic or heteroaromatic ring systems are bonded to the phosphine oxide group. Particular preference is given to ketones and phosphine oxides of the following formulae (12) and (13):

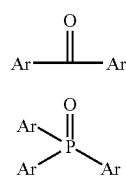

Formula (12)

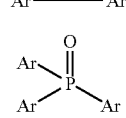

Formula (13)

where Ar has the same meaning as described above.

Particularly suitable ketones are disclosed in the application WO 04/093207. Particularly suitable phosphine oxides, sulfoxides and sulfones are disclosed in the application WO 05/003253. These compounds can be employed particularly well together with the compounds of the formula (1) as matrix material for phosphorescent emitters.

If the compound of the formula (1) is employed together with a ketone, a phosphine oxide, a sulfoxide or a sulfone as matrix material, the ratio of the compound of the formula (1) to the ketone, phosphine oxide, sulfoxide or sulfone is preferably in the range from 10:1 to 1:10, particularly preferably in the range from 5:1 to 1:5, very particularly preferably in the range from 3:1 to 1:3.

In a further preferred embodiment of the invention, the compounds of the formula (1) are employed as hole-transport material or as hole-injection material. The compound is then preferably employed in a hole-transport or hole-injection layer in a fluorescent or phosphorescent OLED. For the purposes of this invention, a hole-injection layer is a layer which is directly adjacent to the anode. For the purposes of this invention, a hole-transport layer is a layer which lies between a hole-injection layer and an emission layer. If the compounds of the formula (1) are used as hole-transport or hole-injection material, it may be preferred for them to be doped with electron-acceptor compounds, for example with $F_4$-TCNQ or with compounds as described in EP 1476881 or EP 1596445.

Preference is furthermore given to an organic electroluminescent device, characterised in that one or more layers are coated by a sublimation method, in which the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electroluminescent device, characterised in that one or more layers are coated by the OVPD (organic vapour phase deposition) method or with the aid of carrier-gas sublimation. The materials are applied here at a pressure between $10^{-5}$ mbar and 1 bar.

Preference is furthermore given to an organic electroluminescent device, characterised in that one or more layers are produced from solution, such as, for example, by spin coating, or using any desired printing process, such as, for example, screen printing, flexographic printing or offset printing, but particularly preferably LITI (light induced thermal imaging, thermal transfer printing) or ink-jet printing. Soluble compounds are necessary for this purpose.

On use in organic electroluminescent devices, the compounds according to the invention have the following surprising advantages over the prior art:

1. The compounds have a significantly higher glass-transition temperature than CBP, which is used in accordance with the prior art as triplet matrix material.
2. The lifetime of the devices is also improved on use of the compounds according to the invention as triplet matrix materials.
3. The efficiency of the devices is furthermore improved on use of the compounds according to the invention as triplet matrix materials.

These above-mentioned advantages are not accompanied by an impairment of the other electronic properties. In particular, the devices according to the invention exhibit the same emission colour as the devices in accordance with the prior art.

The present application text is directed to the use of the compounds according to the invention in relation to OLEDs and PLEDs and the corresponding displays. In spite of this restriction of the description, it is possible for the person skilled in the art, without further inventive step, also to employ the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photoreceptors.

The present invention likewise relates to the use of the compounds according to the invention in the corresponding devices and to these devices themselves.

The invention is explained in greater detail by the following examples without wishing to restrict it thereby.

EXAMPLES

Unless indicated otherwise, the following syntheses are carried out under a protective-gas atmosphere in dried solvents. The starting materials can be obtained from ALDRICH. 4-Bromo-2-nitrobiphenyl and 2'-nitro-p-terphenyl are prepared by the literature method (M. Tavasli et at., *Synthesis* 2005, 1619-1624).

Example 1

General Synthetic Procedure for the Carbazole Synthesis

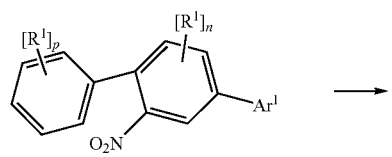

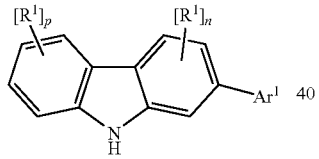

A mixture of 238 mmol of the corresponding nitroaromatic compound and 290.3 ml (1669 mmol) of triethyl phosphite is heated under reflux for 12 h. The remaining triethyl phosphite is subsequently distilled off (72-76° C./9 mmHg). Water/MeOH (1:1) is added to the residue, and the solid is filtered off and recrystallised.

Example 2

General Synthetic Procedure for the Hartwig-Buchwald Coupling

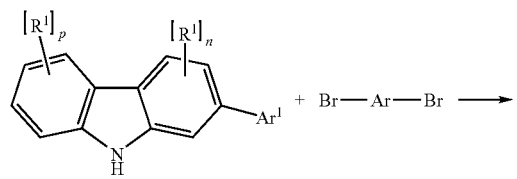

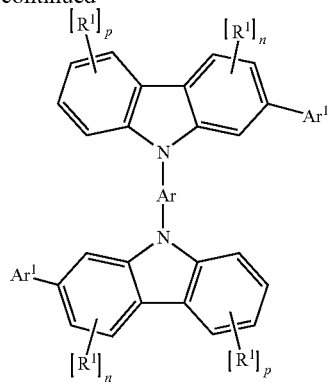

A degassed solution of 176 mmol of the carbazole derivative and 64.2 mmol of the dibromoaromatic compound in 250 ml of xylene is saturated with $N_2$ for 1 h. Firstly 3 ml (12.2 mmol) of $P(^tBu)_3$, then 0.5 g (2.45 mmol) of palladium acetate are then added to the solution, and 81.9 g (956 mmol) of $K_3PO_4$ in the solid state are subsequently added. The reaction mixture is heated under reflux for 18 h. After cooling to room temperature, 1000 ml of water are carefully added. The organic phase is washed with 4×50 ml of $H_2O$ and dried over $MgSO_4$, and the solvents are removed in vacuo. The pure product is obtained by recrystallisation.

Example 3

Synthesis of bis[2-phenylcarbazolyl]biphenyl (C1)

a) Synthesis of 2-phenyl-9H-carbazole

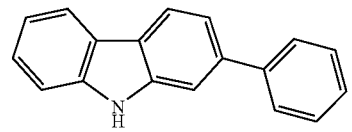 [SMILES: c1ccc(-c2ccc3c(c2)[nH]c2ccccc23)cc1]

The synthesis of this compound is described in the literature (M. Tavasli et al., *Synthesis* 2005, 1619-1624).

b) Reaction with 4,4'-dibromobiphenyl to Give bis[2-phenyl-carbazolyl]biphenyl

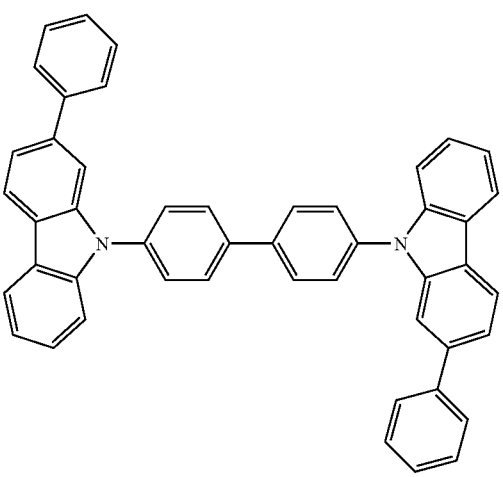

C1

The synthesis is carried out by the general synthetic procedure according to Example 2 using 4,4'-dibromobiphenyl. The solid obtained is washed by stirring with hot dioxane, then with MeOH and subsequently with ethyl acetate; yield: 39 g, 96% of theory; purity: 99.9% according to HPLC.

Example 4

Synthesis of 1,3-bis[2-phenylcarbazolyl]benzene (C2) by Reaction of 2-phenyl-9H-carbazole with 1,3-dibromobenzene

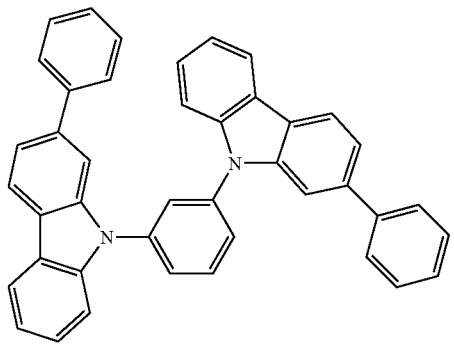

C2

The synthesis is carried out by the general synthetic procedure according to Example 2 using 1,3-dibromobenzene. The solid obtained is recrystallised from hexane/CH$_2$Cl$_2$ (5:1). The deposited crystals are filtered off with suction, washed with a little MeOH and dried in vacuo; yield: 29.5 g, 91% of theory; purity: 99.9% according to HPLC.

Example 5

Synthesis of bis[2-o-tolylcarbazolyl]biphenyl (C3)

a) Synthesis of 2-methyl-2'-nitro-p-terphenyl

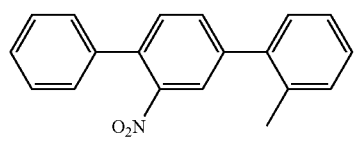 [SMILES: Cc1ccccc1-c1ccc(-c2ccccc2)c([N+](=O)[O-])c1]

1.7 g (1.49 mmol) of Pd(PPh$_3$)$_4$ are added to a well-stirred, degassed suspension of 25 g (183.8 mmol) of o-tolylboronic acid, 51.1 g (183.8 mmol) of 4-bromo-2-nitrobiphenyl and 66.5 g (212.7 mmol) of potassium carbonate in a mixture of 250 ml of water and 250 ml of THF, and the mixture is heated under reflux for 17 h. After cooling, the organic phase is separated off, washed three times with 200 ml of water and once with 200 ml of saturated, aqueous sodium chloride solution, dried over magnesium sulfate and evaporated to dryness in a rotary evaporator. The grey residue is recrystallised from hexane. The deposited crystals are filtered off with suction, washed with a little MeOH and dried in vacuo; yield: 50.5 g, 95% of theory; purity: 99.5% according to HPLC.

b) Synthesis of 2-o-tolyl-9H-carbazole

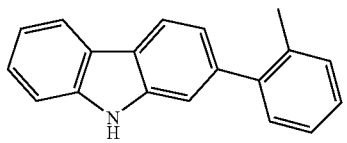 [SMILES: Cc1ccccc1-c1ccc2c(c1)[nH]c1ccccc12]

The synthesis is carried out by the general carbazole synthetic procedure according to Example 1, using the terphenyl derivative from Example 5a). The solid obtained is recrystallised from hexane. The deposited crystals are filtered off with suction, washed with a little MeOH and dried in vacuo; yield: 85 g, 80% of theory; purity: 98.0% according to HPLC.

c) Reaction with 4,4'-dibromobiphenyl to give bis[2-o-tolylcarbazolyl]-biphenyl

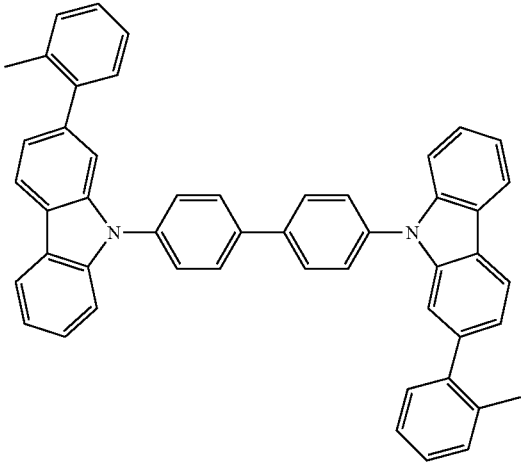

C3

The synthesis is carried out by the general synthetic procedure according to Example 2 using 4,4'-dibromobiphenyl. The solid obtained is recrystallised from hexane/CH$_2$Cl$_2$ (5:1). The deposited crystals are filtered off with suction, washed with a little MeOH and dried in vacuo; yield: 44 g, 94% of theory; purity: 99.9% according to HPLC.

Example 6

Synthesis of bis[5-methyl-2-o-tolylcarbazolyl]biphenyl (C4)

a) Synthesis of 2,2''-dimethyl-2'-nitro-p-terphenyl

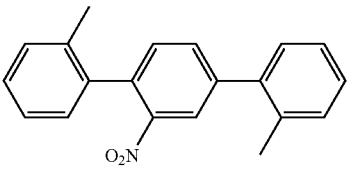 [SMILES: Cc1ccccc1-c1ccc(-c2ccccc2C)c([N+](=O)[O-])c1]

5.46 g (4.7 mmol) of Pd(PPh$_3$)$_4$ are added to a well-stirred, degassed suspension of 155 g (1140 mmol) of o-tolylboronic acid, 133.4 g (474.9 mmol) of 2,5-dibromonitrobenzene and 305.3 g (1435 mmol) of potassium carbonate in a mixture of 250 ml of water and 250 ml of THF, and the mixture is heated under reflux for 20 h. After cooling, the organic phase is separated off, washed three times with 200 ml of water and once with 200 ml of saturated, aqueous sodium chloride solution, dried over magnesium sulfate and evaporated to dryness in vacuo in a rotary evaporator. The grey residue is recrystallised from hexane. The deposited crystals are filtered off with suction, washed with a little MeOH and dried in vacuo; yield: 50.5 g, 97% of theory; purity: 99.2% according to HPLC.

b) Synthesis of 5-methyl-2-o-tolyl-9H-carbazole

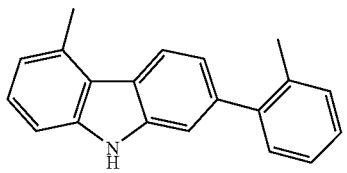 [SMILES: Cc1ccccc1-c1ccc2c(c1)[nH]c1cccc(C)c12]

The synthesis is carried out by the general carbazole synthetic procedure according to Example 1, using the terphenyl derivative from Example 6a). The solid obtained is recrystallised from hexane/CH$_2$Cl$_2$ (5:1). The deposited crystals are filtered off with suction, washed with a little MeOH and dried in vacuo; yield: 76 g, 70% of theory; purity: 97.0% according to HPLC.

c) Reaction with 4,4'-dibromobiphenyl to Give bis[5-methyl-2-o-tolyl-carbazolyl]biphenyl

C4

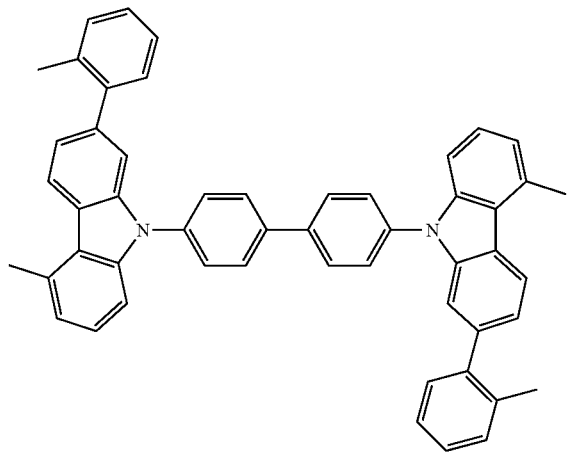

The synthesis is carried out by the general synthetic procedure according to Example 2 using 4,4'-dibromobiphenyl. The solid obtained is recrystallised from hexane/CH$_2$Cl$_2$ (5:1). The deposited crystals are filtered off with suction, washed with a little MeOH and dried in vacuo; yield: 44 g, 90% of theory; purity: 99.9% according to HPLC.

Example 7

Synthesis of bis[2-naphth-1-ylcarbazolyl]biphenyl (C5)

a) Synthesis of 4-naphth-1-yl-2-nitrobiphenyl

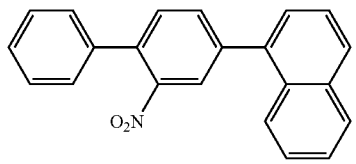 [SMILES: O=[N+]([O-])c1cc(-c2cccc3ccccc23)ccc1-c1ccccc1]

1.62 g (1.40 mmol) of Pd(PPh$_3$)$_4$ are added to a well-stirred, degassed suspension of 46 g (268 mmol) of 1-naphthylboronic acid, 71 g (255.3 mmol) of 4-bromo-2-nitrobiphenyl and 93 g (433.9 mmol) of potassium carbonate in a mixture of 700 ml of water and 700 ml of THF, and the mixture is heated under reflux for 17 h. After cooling, the organic phase is separated off, washed three times with 400 ml of water and once with 400 ml of saturated, aqueous sodium chloride solution, dried over magnesium sulfate and evaporated to dryness in vacuo in a rotary evaporator. The grey residue is recrystallised from hexane. The deposited crystals are filtered off with suction, washed with a little MeOH and dried in vacuo; yield: 83.1 g, 97.9% of theory; purity: 99.0% according to HPLC.

b) Synthesis of 2-naphth-1yl-9H-carbazole

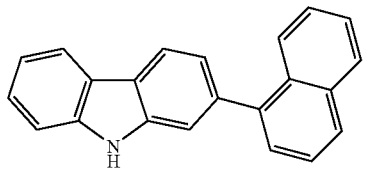 [SMILES: c1ccc2c(-c3ccc4c(c3)[nH]c3ccccc34)cccc2c1]

The synthesis is carried out by the general carbazole synthetic procedure according to Example 1, using the compound from Example 7a). The solid obtained is recrystallised from hexane/CH$_2$Cl$_2$ (5:1). The deposited crystals are filtered off with suction, washed with a little MeOH and dried in vacuo; yield: 55 g, 75% of theory; purity: 97.0% according to HPLC.

c) Reaction with 4,4'-dibromobiphenyl to Give bis[2-naphth-1-yl-carbazolyl]biphenyl

C5

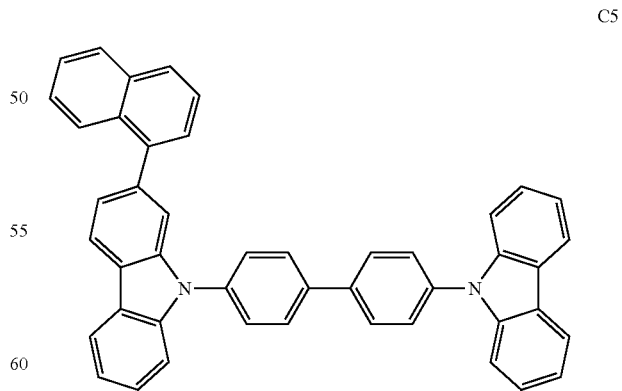

The synthesis is carried out by the general synthetic procedure according to Example 2 using 4,4'-dibromobiphenyl. The solid obtained is recrystallised from hexane/CH$_2$Cl$_2$ (5:1). The deposited crystals are filtered off with suction, washed with a little MeOH and dried in vacuo; yield: 41 g, 85% of theory; purity: 99.9% according to HPLC.

Example 8

Synthesis of bis[9-naphth-1-ylbenzo[c]carbazolyl]biphenyl (C6)

a) Synthesis of 1-nitro-2,5-dinaphth-1-ylbenzene

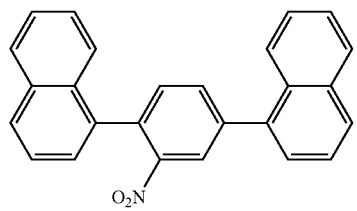 [SMILES: O=[N+]([O-])c1cc(-c2cccc3ccccc23)ccc1-c1cccc2ccccc12]

2.4 g (2.1 mmol) of Pd(PPh$_3$)$_4$ are added to a well-stirred, degassed suspension of 67.8 g (190 mmol) of 1-naphthylboronic acid, 53.3 g (190 mmol) of 2,5-dibromonitrobenzene and 137.9 g (648.5 mmol) of potassium carbonate in a mixture of 250 ml of water and 250 ml of THF, and the mixture is heated under reflux for 20 h. After cooling, the organic phase is separated off, washed three times with 200 ml of water and once with 200 ml of saturated, aqueous sodium chloride solution, dried over magnesium sulfate and evaporated to dryness in vacuo in a rotary evaporator. The grey residue is recrystallised from hexane. The deposited crystals are filtered off with suction, washed with a little MeOH and subsequently dried in vacuo; yield: 86.1 g, 71% of theory; purity: 98.4% according to HPLC.

b) Synthesis of 9-naphth-1-yl-7H-beanzo[c]carbazole

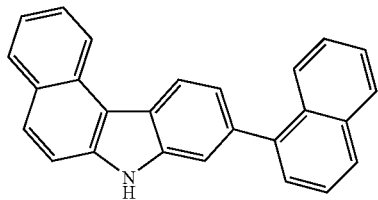 [SMILES: c1ccc2c(-c3ccc4c(c3)[nH]c3ccc5ccccc5c34)cccc2c1]

The synthesis is carried out by the general carbazole synthetic procedure according to Example 1, using the compound from Example 8a). The solid obtained is recrystallised from hexane/CH$_2$Cl$_2$ (5:1). The deposited crystals are filtered off with suction, washed with a little MeOH and subsequently dried in vacuo; yield: 49 g, 60% of theory; purity: 97.9% according to HPLC.

c) Reaction with 4,4'-dibromobiphenyl to Give bis[9-naphthylbenzo[c]-carbazolyl]biphenyl

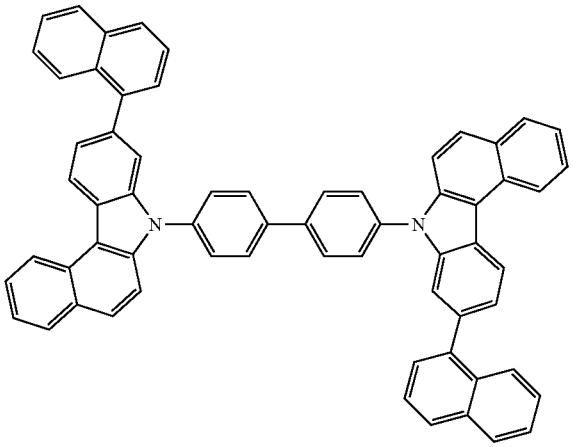

The synthesis is carried out by the general synthetic procedure according to Example 2 using 4,4'-dibromobiphenyl. The solid obtained is recrystallised from hexane/CH$_2$Cl$_2$ (5:1). The deposited crystals are filtered off with suction, washed with a little MeOH and dried in vacuo; yield: 49.5 g, 84% of theory; purity: 99.9% according to HPLC.

Example 9

Determination of the Glass-Transition Temperatures

The glass-transition temperature of compounds C1 to C6 and of CBP (bis-4,4'-(N,N'-carbazolyl)biphenyl) and 1,3-bis (carbazolyl)benzene as comparative compounds is determined. The glass-transition temperature $T_g$ is determined using a DSC instrument from Netsch, DSC 204/1/G Phönix. In each case, 5-10 mg samples are measured. For determination of the glass-transition temperature $T_g$, the sample is removed from the DSC instrument after melting and immediately introduced into liquid nitrogen in order to achieve a maximum cooling rate. The $T_g$ can be determined on fast heating (20 K/min or, if no result is obtained at this heating rate, at 100 K/min). The results are summarised in Table 1 and Table 2. As can be seen, the glass-transition temperatures of the compounds according to the invention are significantly higher than those of the corresponding comparative compounds in which the carbazole groups are not substituted by aryl groups.

TABLE 1

| Glass-transition temperatures | |
|---|---|
| Compound | $T_g$ in ° C. |
| CBP (comparison) | 112-116 |
| C1 | 141 |
| C3 | 132 |
| C4 | |
| C5 | 162 |
| C6 | 198 |

TABLE 2

| Glass-transition temperatures | |
| --- | --- |
| Compound | $T_g$ in ° C. |
| 1,3-dicarbazolylbenzene (comparison) | 66 |
| C2 | 110 |

Example 10

Production and Characterisation of Organic Electroluminescent Devices Which Comprise the Compounds According to the Invention Electroluminescent devices according to the invention can be produced as described, for example, in WO 05/003253. The results for various OLEDs are compared here. The basic structure, the materials used, the degree of doping and layer thicknesses thereof are identical for better comparability. Only the host in the emission layer is varied. The first example describes a comparative standard in accordance with the prior art, in which the emission layer consists of the host material CBP and the guest material (dopant) Ir(piq)$_3$. Furthermore, an OLED having an emitter layer consisting of the host material C1, C2, C4 or C5 and the guest material (dopant) Ir(piq)$_3$ is described. OLEDs having the following structure are produced analogously to the above-mentioned general process;

| | |
| --- | --- |
| Hole-injection layer (HIL) | 10 nm 2,2',7,7'-tetrakis(di-para-tolyl-amino)spiro-9,9'-bifluorene |
| Hole-transport layer (HTL) | 30 nm NPB (N-naphthyl-N-phenyl-4,4'-diaminobiphenyl) |
| Emission layer (EML) | host: CPB (vapour-deposited; from ALDRICH and purified further, sublimed twice; 4,4'-bis(N-carbazolyl)biphenyl) as comparison or C1, C2, C4 or C5. Dopant: Ir(piq)$_3$ (10% doping, vapour-deposited; synthesised in accordance with WO 03/0068526; see Table 3 |
| Hole-blocking layer (HBL) | BAlq 10 nm (purchased from ERay, bis(2-methyl-8-quinolinolato)(para-phenyl-phenolato)aluminium(III)) |
| Electron conductor (ETL) | 20 nm AlQ$_3$ (purchased from ERay, tris-(quinolinato)aluminium(III)) |
| Cathode | 1 nm LiF, 150 nm Al on top. |

The structure of Ir(piq)$_3$ is depicted below for reasons of clarity:

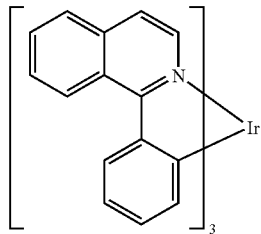

These still unoptimised OLEDs are characterised by standard methods; for this purpose, the electroluminescence spectra, the efficiency (measured in cd/A) as a function of the luminance, calculated from current/voltage/luminance characteristic lines (IUL characteristic lines), and the lifetime are determined.

Use of OLEDs produced using the standard host CBP typically gives a maximum efficiency of about 7.9 cd/A under the conditions described above at colour coordinates of CIE: x=0.68, y=0.32. For the reference luminous density of 1000 cd/m$^2$, voltages of 6.0 V are required. The lifetime is about 5000 h at an initial luminous density of 1000 cd/m$^2$ (see Table 3). By contrast, OLEDs produced using the host materials C1, C2, C4 and C5 according to the invention exhibit maximum efficiencies of 8.3 cd/A at colour coordinates of CIE: x=0.68, y=0.32, with an otherwise identical structure, where the requisite voltage for the reference luminous density of 1000 cd/m$^2$ is up to 5.0 V (see Table 3). The lifetime at an initial luminous density of 1000 cd/m$^2$ is, at up to 11,000 h, longer than with the reference material CBP (see Table 3).

TABLE 3

Device results with host materials according to the invention with Ir(piq)$_3$ as dopant

| Experiment | EML | Max. efficiency [cd/A] | Voltage [V] at 100 cd/m$^2$ | CIE (x, y) | Lifetime [h] initial luminance 1000 [cd/m$^2$] |
| --- | --- | --- | --- | --- | --- |
| Example 11 (comparison) | CBP: 10% of Ir(piq)$_3$ (30 nm) | 7.9 | 6.0 | 0.68/0.32 | 5000 |
| Example 12 | C1: 10% of Ir(piq)$_3$ (30 nm) | 8.3 | 5.9 | 0.68/0.32 | 11000 |
| Example 13 | C2: 10% of Ir(piq)$_3$ (30 nm) | 7.5 | 5.6 | 0.68/0.32 | 7000 |
| Example 14 | C4: 10% of Ir(piq)$_3$ (30 nm) | 8.2 | 5.2 | 0.68/0.32 | 5000 |
| Example 15 | C5: 10% of Ir(piq)$_3$ (30 nm) | 8.1 | 5.0 | 0.68/0.32 | 9000 |

Further organic electroluminescent devices which have the same device structure as the devices mentioned above, but in which Ir(ppy)$_3$ (tris(phenylpyridine)iridium, synthesised in accordance with WO 04/085449) is used as emission material (dopant) were produced analogously to Examples 11 to 15 indicated above.

The structure of Ir(ppy)$_3$ is depicted below for reasons of clarity:

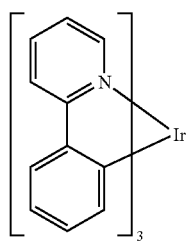

Use of OLEDs produced using the standard host CBP typically gives a maximum efficiency of about 25 cd/A under the conditions described above at colour coordinates of CIE: x=0.30, y=0.60. Voltages of 5.3 V are required for the reference luminous density of 1000 cd/m$^2$. The lifetime is about 2400 h at an initial luminous density of 1000 cd/m$^2$ (see Table 4). By contrast, OLEDs produced using the host C1 according to the invention exhibit maximum efficiencies of 27 cd/A at colour coordinates of CIE: x=0.30, y=0.60, where the requisite voltage for the reference luminous density of 1000 cd/m² is 4.7 V (see Table 4). The lifetime at an initial luminous density of 1000 cd/m² is, at 3000 h, longer than with the reference material CBP (see Table 4).

TABLE 4

Device results with host materials according to the invention with Ir(ppy)₃ as dopant

| Experiment | EML | Max. efficiency [cd/A] | Voltage [V] at 100 cd/m² | CIE (x, y) | Lifetime [h] initial luminance 1000 [cd/m²] |
|---|---|---|---|---|---|
| Example 16 (comparison) | CBP: 5% of Ir(ppy)₃ (30 nm) | 25 | 5.3 | 0.30/0.60 | 2400 |
| Example 17 | C1: 5% of Ir(ppy)₃ (30 nm) | 27 | 4.7 | 0.30/0.60 | 3000 |

A further organic electroluminescent device which has the same device structure and the same emission material Ir(ppy)3 as the device mentioned above, but in which a mixture of compound C1 according to the invention and bis(9,9'-spirobifluoren-2-yl) ketone (synthesised in accordance with WO 04/093207) Is used as matrix material (host material) was produced analogously to Example 17 indicated above.

The structure of bis(9,9'-spirobifluoren-2-yl) ketone is depicted below for reasons of clarity:

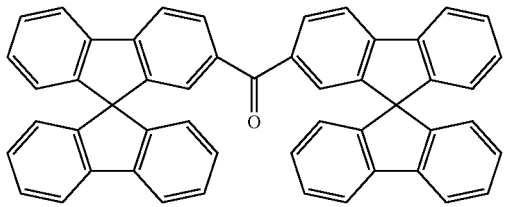 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2]

Use of OLEDs produced using a mixture of host C1 according to the invention and bis(9,9'-spirobifluoren-2-yl) ketone gives maximum efficiencies of 37 cd/A at colour coordinates of CIE: x=0.34, y=0.60, where the requisite voltage for the reference luminous density of 1000 cd/m² is only 3.2 V (see Table 5). The lifetime at an initial luminous density of 1000 cd/m² is 14,000 h (see Table 5). Thus, yet a further increase in the efficiency and lifetime is possible using a mixture of the host materials.

TABLE 5

Device results with host materials according to the invention with Ir(ppy)₃ as dopant

| Experiment | EML | Max. efficiency [cd/A] | Voltage [V] at 100 cd/m² | CIE (x, y) | Lifetime [h] initial luminance 1000 [cd/m²] |
|---|---|---|---|---|---|
| Example 18 | 47.5% of C1, 47.5% of spiroketone 5% of Ir(ppy)₃ (30 nm) | 37 | 3.2 | 0.34/0.60 | 14000 |

The invention claimed is:

1. A compound of the formula (1)

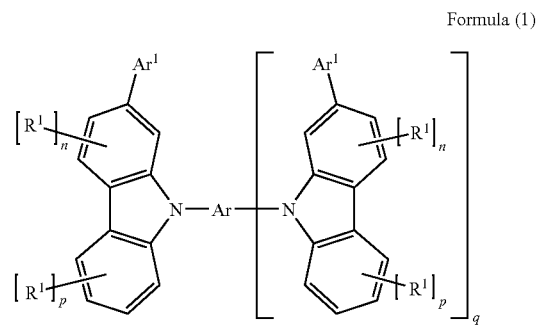

Formula (1)

wherein

Ar is on each occurrence an aromatic or heteroaromatic ring system having 5 to 60 aromatic ring atoms, which is optionally substituted by one or more radicals $R^1$;

$Ar^1$ is on each occurrence, identically or differently, an aromatic or heteroaromatic ring system having 5 to 60 aromatic ring atoms, which is optionally substituted by one or more radicals R;

R is on each occurrence, identically or differently, Cl, Br, I, $N(Ar^2)_2$, CN, $NO_2$, $Si(R^2)_3$, $B(OR^2)_2$, $C(=O)Ar^2$, $P(=O)(Ar^2)_2$, $S(=O)Ar^2$, $S(=O)_2Ar^2$, $-CR^2=CR^2(Ar^2)$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups is optionally replaced by $R^2C=CR^2$, $C\equiv C$, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms is optionally replaced by F, Cl, Br, I, CN or $NO_2$, or an aromatic or heteroaromatic ring system having 5 to 60 aromatic ring atoms, which in each case is optionally substituted by one or more radicals $R^2$, or an aryloxy or heteroaryloxy group having 5 to 60 aromatic ring atoms, which is optionally substituted by one or more radicals $R^2$, or a combination of these systems; two or more substituents R here optionally form a mono- or polycyclic aliphatic or aromatic ring system with one another;

$R^1$ is on each occurrence, identically or differently, R, a group $Ar^1$ or F;

$Ar^2$ is on each occurrence, identically or differently, an aromatic or heteroaromatic ring system having 5 to 60 aromatic ring atoms, which is optionally substituted by one or more radicals $R^2$;

R² is on each occurrence, identically or differently, H or an aliphatic, aromatic or heteroaromatic hydrocarbon radical having 1 to 20 C atoms; two or more substituents R² here optionally form a mono- or polycyclic aliphatic or aromatic ring system with one another;

n is on each occurrence, identically or differently, 0, 1, 2 or 3;

p is on each occurrence, identically or differently, 0, 1, 2, 3 or 4; and q is 1, 2, 3, 4 or 5.

2. The compound according to claim 1, wherein n is identically or differently on each occurrence, are 0 or 1.

3. The compound according to claim 1, wherein n is 0.

4. The compound according to claim 1, wherein the compound is selected from the structures of the formulae (2) to (7)

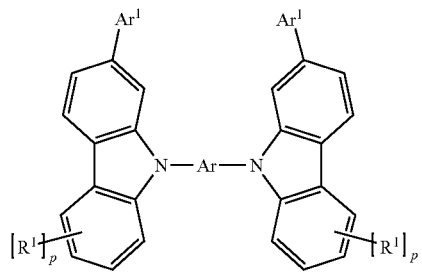

Formula (2)

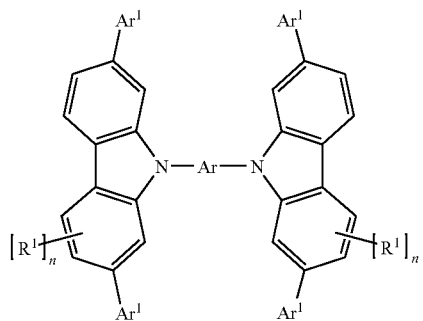

Formula (3)

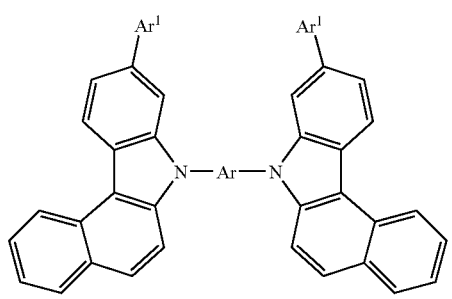

Formula (4)

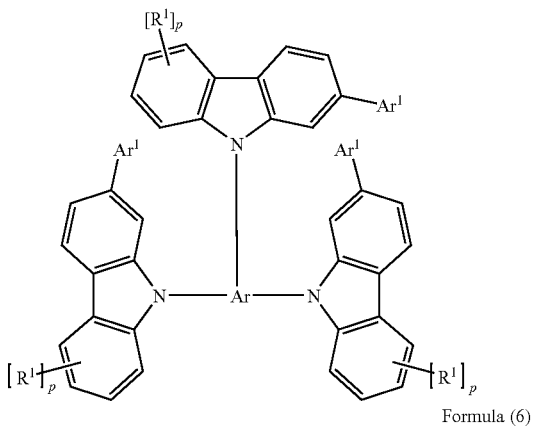

Formula (5)

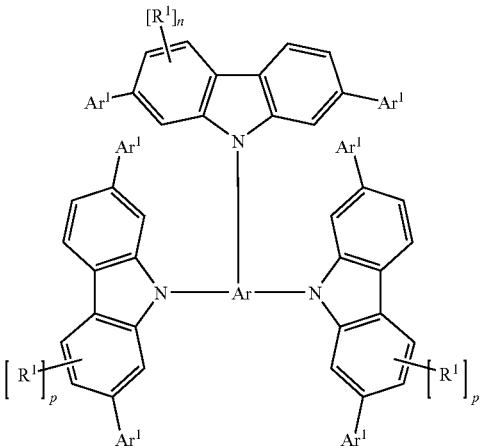

Formula (6)

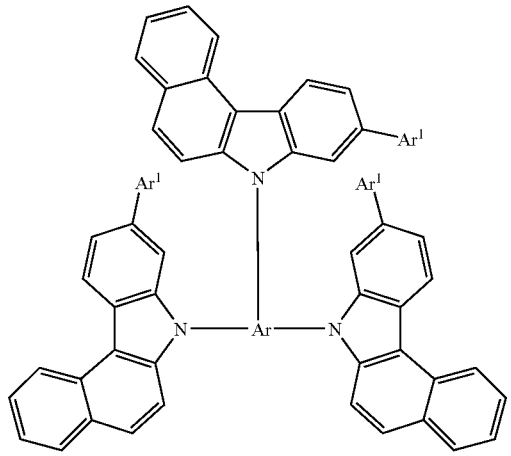

Formula (7)

where symbols and indices have the meanings indicated in claim 1.

5. The compound according to claim 1, wherein p is identically or differently on each occurrence, is 0, 1 or 2.

6. The compound according to claim 1, wherein p is identically or differently on each occurrence, is 0 or 1.

7. The compound according to claim 1, wherein R¹ is bonded in the 5-position or 7-position of the carbazole if the index p =1, or in that the substituents R¹ are bonded in the 5- and 7-position of the carbazole if the index p =2.

8. The compound according to claim 1, wherein Ar is 1,2-phenylene, 1,3-phenylene, 1,4-phenylene, 1,3,5-benzene, 3,3'-biphenyl, 4,4'-biphenyl, 1,3,5-triphenylbenzene, triphenylamine, 2,7-fluorenylene, which is optionally substituted by one or more radicals $R^1$, 2,7-spirobifluorenylene, which is optionally substituted by one or more radicals $R^1$, indenofluorenylene, which is optionally substituted by one or more radicals $R^1$, 4,4'''-(1,1':2',1'',2'',1'''-quaterphenyl), 4,4'-(2,2'-dimethylbiphenyl), 4,4'-(1,1'-binaphthyl), 4,4'-stilbenyl or dihydrophenanthrenyl, which is optionally substituted by one or more radicals $R^1$.

9. The compound according to claim 1, wherein $Ar^1$ is identically or differently, phenyl, 1-naphthyl, 2-naphthyl, triphenylamine, 2-carbazolyl, 3-carbazolyl, 9-carbazolyl, naphthyldiphenylamine or dinaphthylphenylamine, each of which is optionally substituted by one or more radicals R.

10. The compound according to claim 1, wherein R is identically or differently on each occurrence, H, $N(Ar^2)_2$, a straight-chain alkyl group having 1 to 5 C atoms or branched alkyl group having 3 to 5 C atoms, where in each case one or more non-adjacent $CH_2$ groups is optionally replaced by $-R^2C=CR^2-$ or $-O-$ and where one or more H atoms is optionally replaced by F, or an aryl group having 6 to 16 C atoms or a heteroaryl group having 2 to 16 C atoms or a spirobifluorene group, each of which is optionally substituted by one or more radicals $R^2$, or a combination of two of these systems.

11. The compound according to claim 1, wherein the compound is a symmetrical compound in which all symbols $Ar^1$ are identical.

12. A process for the preparation of the compound according to claim 1 which comprises reacting a 4-aryl-2-nitro-1,1'-biphenyl or 4-heteroaryl-2-nitro-1,1'-biphenyl, where the aryl or heteroaryl group is optionally substituted by one or more radicals R and the biphenyl is optionally substituted by one or more radicals $R^1$, with a trialkyl phosphite, where the alkyl groups, identically or differently on each occurrence, have 1 to 10 C atoms, to give the corresponding carbazole, followed by a Hartwig-Buchwald coupling to an aromatic compound Ar which has at least two reactive groups.

13. The process as claimed in claim 12, wherein the two reactive groups are chlorine, bromine, iodine, triflate, tosylate or $OSO_2-R^2$, wherein $R^2$ is on each occurrence, identically or differently, H or an aliphatic, aromatic or heteroaromatic hydrocarbon radical having 1 to 20 C atoms; two or more substituents $R^2$ here optionally form a mono- or polycyclic aliphatic or aromatic ring system with one another.

14. An organic electronic device comprising at least one compound according to claim 1 in at least one layer.

15. The organic electronic device according to claim 14, wherein the device is an electroluminescent device comprising a cathode, an anode and at least one emitting layer and optionally further layers, selected from one or more hole-injection layers, hole-transport layers, hole-blocking layers, electron-transport layers, electron-injection layers and/or charge-generation layers.

16. The organic electronic device according to claim 14, wherein the device is an electroluminescent device and wherein said at least one compound is employed as matrix for phosphorescent dopants.

17. The organic electronic device according to claim 14, wherein the device is an electroluminescent device and wherein said at least one compound is employed together with an aromatic ketone, an aromatic phosphine oxide, an aromatic sulfoxide or an aromatic sulfone as matrix for a phosphorescent dopant.

18. The organic electroluminescent device according to claim 17, wherein said phosphorescent dopant comprises at least one compound which emits light on suitable excitation and contains at least one atom having an atomic number of greater than 20.

19. The organic electroluminescent device according to claim 17, wherein said phosphorescent dopant comprises at least one compound which emits light on suitable excitation and contains at least one atom having an atomic number of greater 38 and less than 84.

20. The organic electronic device according to claim 14, wherein the device is an electroluminescent device and wherein said at least one compound is employed as hole-transport material or as hole-injection material.

21. The compound according to claim 1, wherein Ar and $Ar^1$ are
    a) aromatic ring systems built up from phenyl or naphthyl groups or both phenyl and naphythyl groups,
    b) linked systems of aromatic ring systems built up from phenyl or naphthyl groups or both phenyl and naphythyl groups,
    c) heteroaromatic groups having not more than two condensed aromatic or heteroaromatic rings,
    d) linked systems of heteroaromatic groups having not more than two condensed aromatic or heteroaromatic rings or
    e) carbazole.

22. The organic electronic device according to claim 14, wherein the device is an organic electroluminescent device, organic field-effect transistor, organic thin-film transistor, organic light-emitting transistor, organic integrated circuit, organic solar cell, organic field-quench device, light-emitting electrochemical cell, organic laser diode or organic photoreceptor.

* * * * *